US012594362B2

(12) United States Patent
Wang et al.

(10) Patent No.: US 12,594,362 B2
(45) Date of Patent: Apr. 7, 2026

(54) MEDICAL IMPLANT WITH CONTROLLABLE ELECTRO-MECHANICAL INTERACTIONS AT A MATERIAL/BACTERIA INTERFACE

(71) Applicant: City University of Hong Kong, Hong Kong (HK)

(72) Inventors: Guomin Wang, Hong Kong (HK); Paul Kim Ho Chu, Hong Kong (HK); Kaiwei Tang, Hong Kong (HK); Zheyi Meng, Shanghai (CN)

(73) Assignee: City University of Hong Kong, Hong Kong (HK)

( * ) Notice: Subject to any disclaimer, the term of this patent is extended or adjusted under 35 U.S.C. 154(b) by 710 days.

(21) Appl. No.: 17/983,338

(22) Filed: Nov. 8, 2022

(65) Prior Publication Data

US 2023/0226254 A1 Jul. 20, 2023

Related U.S. Application Data

(60) Provisional application No. 63/300,269, filed on Jan. 18, 2022.

(51) Int. Cl.
| | |
|---|---|
| *A61L 27/30* | (2006.01) |
| *A61B 17/58* | (2006.01) |
| *A61L 31/16* | (2006.01) |

(52) U.S. Cl.
CPC ............ *A61L 27/306* (2013.01); *A61L 31/16* (2013.01)

(58) Field of Classification Search
CPC ......... A61B 17/70; A61B 17/80; A61B 17/86; A61B 17/88; A61L 27/306; A61L 31/16

USPC ....... 606/70–71, 76, 280–299, 300–331, 907
See application file for complete search history.

(56) References Cited

U.S. PATENT DOCUMENTS

| | | | | |
|---|---|---|---|---|
| 5,509,933 | A * | 4/1996 | Davidson | A61L 31/022 |
| | | | | 606/301 |
| 6,882,051 | B2 * | 4/2005 | Majumdar | H10D 62/118 |
| | | | | 257/734 |
| 9,784,888 | B2 * | 10/2017 | Naik | B32B 9/00 |
| 11,116,877 | B2 * | 9/2021 | Gifford | B81C 1/00206 |
| 2002/0111694 | A1 * | 8/2002 | Ellingsen | A61L 27/047 |
| | | | | 623/23.57 |

(Continued)

OTHER PUBLICATIONS

C. Caleman, D. van der Spoel, Picosecond melting of ice by an infrared laser pulse: a simulation study. Angew. Chem. Int. Ed. 47, 1439-1442 (2008).

(Continued)

*Primary Examiner* — Jessica Weiss
(74) *Attorney, Agent, or Firm* — Idea Intellectual Limited; Sam T. Yip

(57) ABSTRACT

An antibacterial implantable medical device or medical material. The surface of an implantable medical device or medical material has a titanium coating formed thereon. Titanium nitride nanowires are formed that extend from the titanium coating at a selected angle to exert a mechanical force on bacteria bilayer membranes sufficient to at least partially disrupt the bacteria bilayer membranes. In one aspect, the titanium nitride nanowires are formed from grown titanium dioxide nanowires by converting the titanium dioxide nanowires to titanium nitride in a heated nitrogen-containing environment. The titanium nitride nanowires are optionally charged to further enhance antibacterial properties.

12 Claims, 52 Drawing Sheets

(56) References Cited

U.S. PATENT DOCUMENTS

| | | | | |
|---|---|---|---|---|
| 2003/0074003 | A1* | 4/2003 | Deslauriers | A61B 17/861 606/308 |
| 2005/0221072 | A1* | 10/2005 | Dubrow | A61L 27/3821 428/292.1 |
| 2007/0282247 | A1* | 12/2007 | Desai | A61L 27/54 604/19 |
| 2008/0306554 | A1* | 12/2008 | McKinley | A61B 17/8605 606/76 |
| 2010/0076497 | A1* | 3/2010 | Zwirkoski | A61B 17/7097 606/301 |
| 2016/0015483 | A1* | 1/2016 | Kumar | C04B 41/4582 606/301 |
| 2017/0174848 | A1* | 6/2017 | Gifford | C30B 33/10 |
| 2018/0272047 | A1* | 9/2018 | Gifford | B82B 3/0019 |
| 2021/0228323 | A1* | 7/2021 | Esquivel-Upshaw | A61C 8/0013 |

OTHER PUBLICATIONS

S. E. Feller, R. W. Pastor, Constant surface tension simulations of lipid bilayers: The sensitivity of surface areas and compressibilities. J. Chem. Phys. 111, 1281-1287 (1999).

M. Doktorova, M. V. LeVine, G. Khelashvili, H. Weinstein, A new computational method for membrane compressibility: Bilayer mechanical thickness revisited. Biophys. J. 116, 487-502 (2019).

W. M. Botello-Smith, W. Jiang, H. Zhang, A. D. Ozkan, Y. C. Lin, C. N. Pham, J. J. Lacroix, Y. Luo, A mechanism for the activation of the mechanosensitive Piezo1 channel by the small molecule Yoda1. Nat. Commun. 10, 4503 (2019).

H. Murata, R. R. Koepsel, K. Matyjaszewski, A. J. Russell, Permanent, non-leaching antibacterial surfaces—2: How high density cationic surfaces kill bacterial cells. Biomaterials 28, 4870-4879 (2007).

J. Hasan, R. J. Crawford, E. P. Ivanova, Antibacterial surfaces: the quest for a new generation of biomaterials. Trends Biotechnol. 31, 295-304 (2013).

D. P. Linklater, V. A. Baulin, X. Le Guevel, J. B. Fleury, E. Hanssen, T. H. P. Nguyen, S. Juodkazis, G. Bryant, R. J. Crawford, P. Stoodley, Antibacterial action of nanoparticles by lethal stretching of bacterial cell membranes. Adv. Mater. 32, 2005679 (2020).

S. Mo, B. Mehrjou, K. Tang, H. Wang, K. Huo, A. M. Qasim, G. Wang, P. K. Chu, Dimensional-dependent antibacterial behavior on bioactive micro/nano polyetheretherketone (PEEK) arrays. Chem. Eng. J. 392, 123736 (2019).

B. Mehrjou, S. Mo, D. Dehghan-Baniani, G. Wang, A. M. Qasim, P. K. Chu, Antibacterial and cytocompatible nanoengineered silk-based materials for orthopedic implants and tissue engineering. ACS Appl. Mater. Interfaces 11, 31605-31614 (2019).

S. Khalid, A. Gao, G. Wang, P. K. Chu, H. Wang, Tuning surface topographies on biomaterials to control bacterial infection. Biomater. Sci. 8, 6840-6857 (2020).

E.-J. Kim, M. Choi, H. Y. Park, J. Y. Hwang, H.-E. Kim, S. W. Hong, J. Lee, K. Yong, W. Kim, Thorn-like TiO 2 nanoarrays with broad spectrum antimicrobial activity through physical puncture and photocatalytic action. Scientific reports 9, 1-12 (2019).

X. Lu, X. Feng, J. R. Werber, C. Chu, I. Zucker, J.-H. Kim, C. O. Osuji, M. Elimelech, Enhanced antibacterial activity through the controlled alignment of graphene oxide nanosheets. Proc. Natl. Acad. Sci. U. S. A. 114, 9793-9801 (2017).

G. Wang, W. Jiang, S. Mo, L. Xie, Q. Liao, L. Hu, Q. Ruan, K. Tang, B. Mehrjou, M. Liu, L. Tong, H. Wang, J. Zhuang, G. Wu, P. K. Chu, Nonleaching Antibacterial Concept Demonstrated by In Situ Construction of 2D Nanoflakes on Magnesium. Adv. Sci. 7, 1902089 (2020).

G. Wang, W. Jin, A. M. Qasim, A. Gao, X. Peng, W. Li, H. Feng, P. K. Chu, Antibacterial effects of titanium embedded with silver nanoparticles based on electron-transfer-induced reactive oxygen species. Biomaterials 124, 25-34 (2017).

R. A. Marcus, Electron transfer reactions in chemistry. Theory and experiment. Rev. Mod. Phys. 65, 599-609 (1993).

G. Wang, H. Feng, L. Hu, W. Jin, Q. Hao, A. Gao, X. Peng, W. Li, K.-Y. Wong, H. Wang, An antibacterial platform based on capacitive carbon-doped TiO2 nanotubes after direct or alternating current charging. Nat. Commun. 9, 2055 (2018).

M. Michalska, F. Gambacorta, R. Divan, I. S. Aranson, A. Sokolov, P. Noirot, P. D. Laible, Tuning antimicrobial properties of biomimetic nanopatterned surfaces. Nanoscale 10, 6639-6650 (2018).

Y. Li, X. Xu, X. Liu, B. Li, Y. Han, Y. Zheng, D. f. Chen, K. W. K. Yeung, Z. Cui, Z. Li, Photoelectrons Mediating Angiogenesis and Immunotherapy through Heterojunction Film for Noninvasive Disinfection. Adv. Sci. 7, 2000023 (2020).

J. Jenkins, J. Mantell, C. Neal, A. Gholinia, P. Verkade, A. H. Nobbs, B. Su, Antibacterial effects of nanopillar surfaces are mediated by cell impedance, penetration and induction of oxidative stress. Nat. Commun. 11, 1626 (2020).

C. M. Bhadra, M. Werner, V. A. Baulin, V. K. Truong, M. A. Kobaisi, S. H. Nguyen, A. Balcytis, S. Juodkazis, J. Y. Wang, D. E. Mainwaring, R. J. Crawford, E. P. Ivanova, Subtle variations in surface properties of black silicon surfaces influence the degree of bactericidal efficiency. Nanomicro Lett. 10, 36 (2018).

W. E. Thomas, E. Trintchina, M. Forero, V. Vogel, E. V. Sokurenko, Bacterial Adhesion to Target Cells Enhanced by Shear Force. Cell 109, 913-923 (2002).

E. P. Ivanova, J. Hasan, H. K. Webb, V. K. Truong, G. S. Watson, J. A. Watson, V. A. Baulin, S. Pogodin, J. Y. Wang, M. J. Tobin, Natural bactericidal surfaces: mechanical rupture of Pseudomonas aeruginosa cells by cicada wings. Small 8, 2489-2494 (2012).

E. P. Ivanova, J. Hasan, H. K. Webb, G. Gervinskas, S. Juodkazis, V. K. Truong, A. H. Wu, R. N. Lamb, V. A. Baulin, G. S. Watson, J. A. Watson, D. E. Mainwaring, R. J. Crawford, Bactericidal activity of black silicon. Nat. Commun. 4, 2838 (2013).

J. Xu, K. Qu, J. Zhao, X. Jian, Z. Gao, J. Xu, Y.-Y. Song, In situ monitoring of the "point discharge" induced antibacterial process by the onsite formation of a Raman probe. Anal. Chem. 92, 2323-2330 (2019).

C. D. Bandara, S. Singh, I. O. Afara, A. Wolff, T. Tesfamichael, K. Ostrikov, A. Oloyede, Bactericidal effects of natural nanotopography of dragonfly wing on *Escherichia coli*. ACS Appl. Mater. Interfaces 9, 6746-6760 (2017).

G. Hazell, P. W. May, P. Taylor, A. H. Nobbs, C. Welch, B. Su, Studies of black silicon and black diamond as materials for antibacterial surfaces. Biomater. Sci. 6, 1424-1432 (2018).

G. Reguera, K. D. McCarthy, T. Mehta, J. S. Nicoll, M. T. Tuominen, D. R. Lovley, Extracellular electron transfer via microbial nanowires. Nature 435, 1098-1101(2005).

T. Lin, I.-W. Chen, F. Liu, C. Yang, H. Bi, F. Xu, F. Huang, Nitrogen-doped mesoporous carbon of extraordinary capacitance for electrochemical energy storage. Science 350, 1508-1513 (2015).

D. Zhang, W. Liu, L. Tang, K. Zhou, H. Luo, High performance capacitors via aligned TiO2 nanowire array. Appl. Phys. Lett. 110, 133902 (2017).

R. S. Friedlander, H. Vlamakis, P. Kim, M. Khan, R. Kolter, J. Aizenberg, Bacterial flagella explore microscale hummocks and hollows to increase adhesion. Proc. Natl. Acad. Sci. U.S.A. 110, 5624-5629 (2013).

M. Cloutier, D. Mantovani, F. Rosei, Antibacterial coatings: challenges, perspectives, and opportunities. Trends Biotechnol. 33, 637-652 (2015).

A. Razatos, Y.-L. Ong, M. M. Sharma, G. Georgiou, Molecular determinants of bacterial adhesion monitored by atomic force microscopy. Proc. Natl. Acad. Sci. U.S.A. 95, 11059-11064 (1998).

A. Labernadie, C. Thibault, C. Vieu, I. Maridonneau-Parini, G. M. Charrière, Dynamics of podosome stiffness revealed by atomic force microscopy. Proc. Natl. Acad. Sci. U.S.A. 107, 21016-21021 (2010).

D. J. Müller, Y. F. Dufrène, Atomic force microscopy as a multifunctional molecular toolbox in nanobiotechnology. Nat. Nanotechnol. 3, 261-269 (2008).

E. R. Rojas, G. Billings, P. D. Odermatt, G. K. Auer, L. Zhu, A. Miguel, F. Chang, D. B. Weibel, J. A. Theriot, K. C. Huang, The

(56)         References Cited

OTHER PUBLICATIONS outer membrane is an essential load-bearing element in Gram-negative bacteria. Nature 559, 617-621 (2018).

B. Bhushan, Springer Handbook of Nanotechnology. Springer, 2017.

M. A. A. Ayee, I. Levitan, Membrane stiffening in osmotic swelling: analysis of membrane tension and elastic modulus. Curr. Top. Membr. 81, 97-123 (2018).

A. Tripathy, P. Sen, B. Su, W. H. Briscoe, Natural and bioinspired nanostructured bactericidal surfaces. Adv. Colloid Interface Sci. 248, 85-104 (2017).

K. Nowlin, A. Boseman, A. Covell, D. LaJeunesse, Adhesion-dependent rupturing of Saccharomyces cerevisiae on biological antimicrobial nanostructured surfaces. Journal of the Royal Society Interface 12, 20140999 (2015).

H. Strahl, L. W. Hamoen, Membrane potential is important for bacterial cell division. Proc. Natl. Acad. Sci. U.S.A. 107, 12281-12286 (2010).

B. E. Logan, Exoelectrogenic bacteria that power microbial fuel cells. Nature Reviews Microbiology 7, 375-381 (2009).

T. A. Taton, Boning up on biology. Nature 412, 491-492 (2001).

S. F. Lamolle, M. Monjo, M. Rubert, H. J. Haugen, S. P. Lyngstadaas, J. E. Ellingsen, The effect of hydrofluoric acid treatment of titanium surface on nanostructural and chemical changes and the growth of MC3T3-E1 cells. Biomaterials 30, 736-742 (2009).

A. G. Gristina, M. Oga, L. X. Webb, C. D. Hobgood, Adherent bacterial colonization in the pathogenesis of osteomyelitis. Science 228, 990-993 (1985).

J. Liu, D. A. Sonshine, S. Shervani, R. H. Hurt, Controlled release of biologically active silver from nanosilver surfaces. ACS Nano 4, 6903-6913 (2010).

G. Wang, K. Tang, Z. Meng, P. Liu, S. Mo, B. Mehrjou, H. Wang, X. Liu, Z. Wu, P. K. Chu, A quantitative bacteria monitoring and killing platform based on electron transfer from bacteria to a semiconductor. Adv. Mater. 32, e2003616 (2020).

A. H. Phakatkar, E. Firlar, L. Alzate, B. Song, S. Narayanan, R. Rojaee, T. Foroozan, R. Deivanayagam, D. J. Banner, R. Shahbazian-Yassar, TEM studies on antibacterial mechanisms of black phosphorous nanosheets. International journal of nanomedicine 15, 3071-3085 (2020).

M. I. Ishak, X. Liu, J. Jenkins, A. H. Nobbs, B. Su, Protruding nanostructured surfaces for antimicrobial and osteogenic titanium implants. Coatings 10, 756 (2020).

T. Y. Ma, J. L. Cao, M. Jaroniec, S. Z. Qiao, Interacting carbon nitride and titanium carbide nanosheets for high-performance oxygen evolution. Angew. Chem. Int. Ed. 128, 1150-1154 (2016).

D. J. Novo, N. G. Perlmutter, R. H. Hunt, H. M. Shapiro, Multiparameter flow cytometric analysis of antibiotic effects on membrane potential, membrane permeability, and bacterial counts of Staphylococcus aureus and Micrococcus luteus. Antimicrob. Agents Chemother. 44, 827-834 (2000).

L. Agosta, E. G. Brandt, A. P. Lyubartsev, Diffusion and reaction pathways of water near fully hydrated TiO2 surfaces from ab initio molecular dynamics. J. Chem. Phys. 147, 024704 (2017).

M. Schneemilch, N. Quirke, Free energy of adhesion of lipid bilayers on titania surfaces. J. Chem. Phys. 151, 134707 (2019).

J. Klauda, R. Venable, J. Freites, Update of the CHARMM all-atom additive force field for lipids: validation on six lipid types. J. Phys. Chem. B 114, 7830-7843 (2010).

J. Essman, L. Perera, M. Berkowitz, T. Darden, H. Lee, L. Pedersen, A smooth particle mesh ewald potential. J. Chem. Phys 103, 8577-8592 (1995).

* cited by examiner

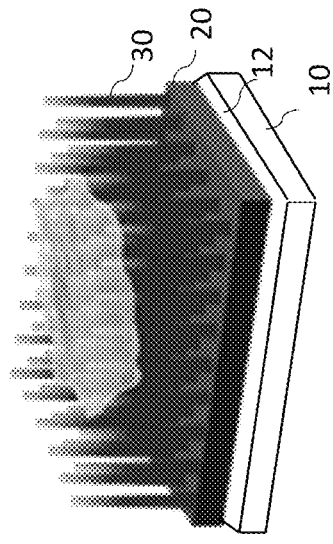
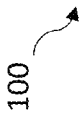
FIG. 1H

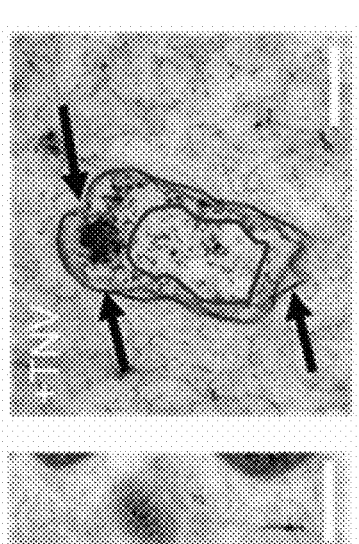
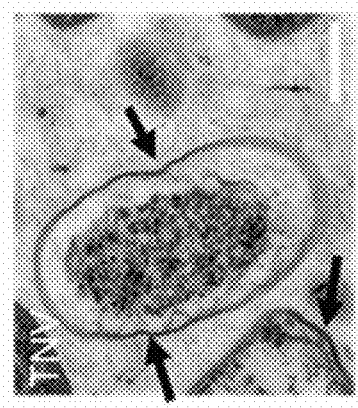
FIG. 5C

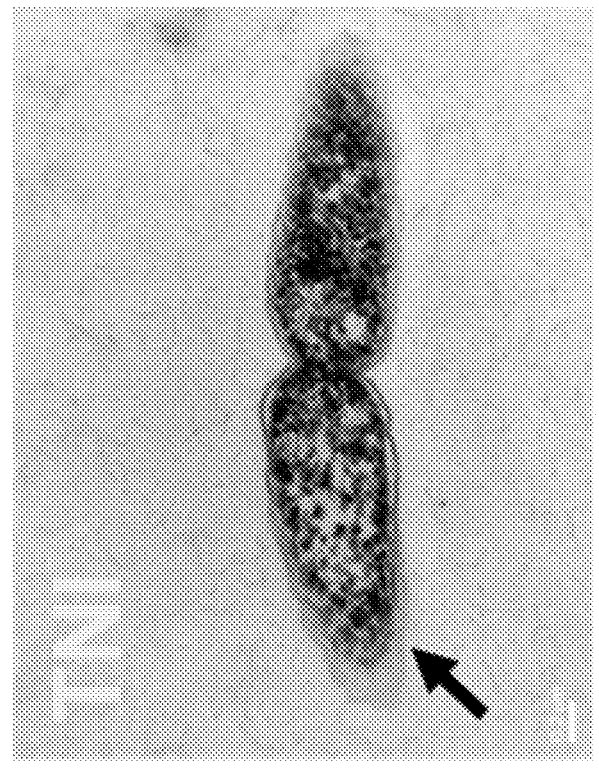
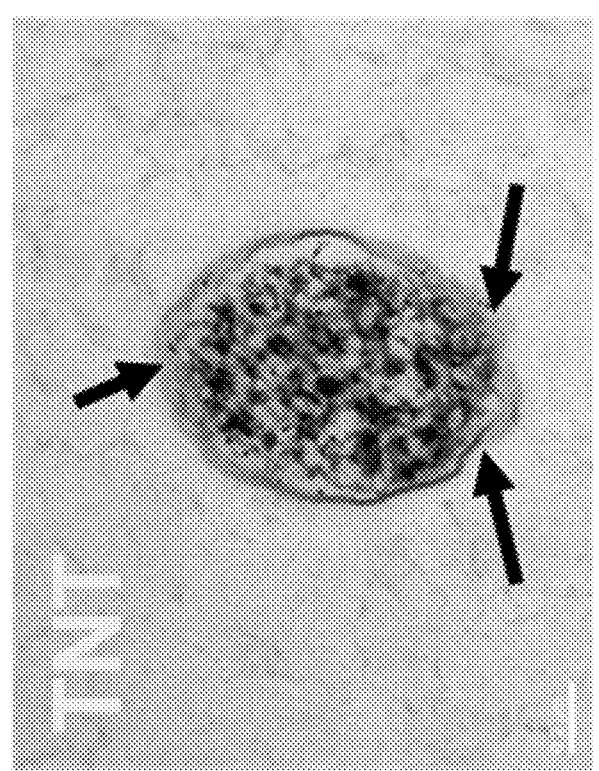
FIG. 16

MEDICAL IMPLANT WITH CONTROLLABLE ELECTRO-MECHANICAL INTERACTIONS AT A MATERIAL/BACTERIA INTERFACE

CROSS-REFERENCE TO RELATED APPLICATIONS

This application claims priority to U.S. Provisional Patent Application 63/300,269 filed 18 Jan. 2022, the disclosure of which is incorporated by reference herein.

FIELD OF THE INVENTION

The present invention relates to implantable medical materials and devices and, more particularly, to surface-modified implantable medical materials and devices with antibacterial properties.

BACKGROUND

The global medical implant market size demonstrates a compound annual growth rate of 7.7% and it will increase to about 170 billion dollars in the coming two years. With an aging world population, growing healthcare access, and advanced technology, Asia-pacific is the fastest growing region. However, implant infection is a common problem which in both high and low income countries. The global implant infection rate is about 5% and has been on increasing trend over the past 50 years. Implant infection can lead to system infection of the patient and/or malfunction of the medical implant. Infection may require removal of the implant and replacement with a new implant or other revision surgery.

Coating strategies have been proposed to prevent implant infection. Generally, antibacterial surfaces can be categorized as leaching ones for planktonic bacteria and non-leaching ones for adhered bacteria by physical interactions. As infections initiate from bacteria adherence on the implant surface and leaching surfaces require replenishment of anti-bacterial agents, and non-leaching surfaces which kill bacteria upon contact based on physical interactions without exhaustion or disturbance in the distal tissue. Antibacterial coatings that are leaching coatings grafted with antibiotics suffer from drawbacks such as systemic toxicity, the need for antibiotic replenishment, uncontrollability, and antimicrobial resistance. Antimicrobial resistance is such a serious global issue that it may become a leading cause of death in 2050, killing at least 1 person every 3 seconds. Hence, there is a need in the art for new coating strategies for medical devices and medical implants to overcome the above drawbacks. The present invention addresses this need.

SUMMARY OF THE INVENTION

The present invention provides a non-leaching antibacterial coating and medical devices with antibacterial coatings that has no systemic effects, kills bacteria more precisely and needs no replenishment. Further, a coating that is amenable to remote control may also be useful in helping to fulfil on-demand treatment. The present invention provides a coating in which physical interactions kill bacteria on contact without leaching.

Non-leaching antibacterial mechanisms based on physical interactions can help prevent bacterial infection on implant materials after surgery; compared to conventional surfaces leaching antibiotics or other agents, there are few systemic side effects and no drug resistance. Moreover, there is no need to replenish the anti-bacterial agents; these agents can be toxic in high quantities. Physical processes such as mechanical forces and electrical interactions can both contribute to bacterial reduction. For instance, sharp edges on surfaces can induce membrane stress in bacteria upon contact resulting in membrane collapse and eventual death.

Extracellular electron transfer (EET) is another means to eliminate bacteria. Electron transfer takes place both on non-insulators and in the respiratory chain of micro-organisms; electron transfer produces electron exchange as a result of the potential difference at the bacteria-materials interface. Previous studies by the present inventors demonstrates that an antibacterial platform based on positively charged capacitive coatings exhibits antibacterial effects. However, previous studies on non-leaching antibacterial surfaces usually consider feasibility, rarely involving a clear quantifiable relationship or the antibacterial mechanism. Antibacterial efficiency is another critical issue determining the clinical practicality of any implant candidate. For instance, antibacterial surfaces with an antibacterial efficiency of 80%, which are commonly deemed acceptable, can only reduce the bacteria population from 5 million to 1 million, for example, but if left alone for 40 min, millions of bacteria can "regrow," causing serious infection. Hence, a more effective surface that can kill more bacteria by simply tuning the physical stress is highly desirable in preventing infection.

Although bacteria can resist surface tension created by the flow of saliva or blood (up to 10 dynes $cm^{-2}$), a sufficiently large force can destroy the bacteria. While it has been shown that micro/nano structures can kill bacteria by contact stress, the antibacterial effects rely more on the random and passive contact between the bacteria and surface, and only a small number of the adhered bacteria are usually killed. Further, electrostatic interactions on a positively charged surface can supplement mechanical forces to kill bacteria. In fact, electron transfer at the interface can alone disrupt the metabolism of bacteria. Hence, a charged capacitive surface with the desirable micro/nano structure may eliminate bacteria more effectively than using a single strategy.

Beyond the mechanism of bacteria destruction, it is important to derive the quantitative relationship between these parameters and bacteria-killing efficacy and elucidate the underlying mechanism in order to exploit a controllable antibacterial surface and to obtain a universal biophysical principle for future antibacterial materials design.

In one aspect, the present invention provides an antibacterial implantable medical device or medical material. An implantable medical device or medical material with a surface has a titanium coating formed thereon. Titanium nitride nanowires extend from the titanium coating on the implantable medical device or medical material. The titanium nitride nanowires extend at a selected angle from the titanium coating such that they are configured to exert a mechanical and/or electrical force on bacteria bilayer membranes sufficient to at least partially disrupt the bacteria bilayer membranes.

In another aspect, the present invention provides a method for forming an antibacterial implantable medical device or medical material. An implantable medical device or medical material having a surface is provided. A titanium coating is formed on the implantable medical device or medical material. Titanium dioxide nanowires are grown on the titanium coating. The titanium dioxide nanowires are converted to titanium nitride nanowires by treatment with a nitrogen-containing gas. The titanium nitride nanowires are grown such that they extend at a selected angle from the titanium coating and are configured to exert a mechanical and/or electrical force on bacteria bilayer membranes sufficient to at least partially disrupt the bacteria bilayer membranes.

The capacitive titanium nitride nanowires (TN) are fabricated with an adjustable topography to exert mechanical and/or electrical stress on bacteria. Progressively increasing antibacterial efficiency is observed in the order of tiled TN (TNT)<inclined TN (TNI)<vertical TN (TNV)<positively charged TNV (+TNV). The bacteria-killing rate increases from a mere 0.7 log reduction on TNV to 3 log reduction on +TNV. In vitro/vivo experiments and theoretical simulation quantitatively reveal that the charged samples can on one hand enhance a closer bacterial attachment to the rugged topography formed by the nanowires leading to a violent piercing effect, and additionally, trigger the electron transfer at the interface disturbing the membrane potential and resulting in the intracellular electron-light region. The above dual effects cause a brittle membrane and a reactive oxygen species (ROS) burst in the bacteria, demonstrates no bacterial infection in vivo on tested implants.

BRIEF DESCRIPTION OF THE DRAWINGS

FIGS. 1A-1H depict sample fabrication and characterization. FIG. 1A is a schematic diagram illustrating the synthesis of TN nanowires with different orientations; FIG. 1B shows morphologies of different samples by SEM with the orientation of the nanowires indicated by red arrows in the insets (scale bar=500 nm); FIG. 1C-1D show high-resolution spectra of Ti 2p of TOV (FIG. 1C) and TNV (FIG. 1D) indicating nitrogen incorporation; FIG. 1E shows XPS depth profiles showing the distribution of Ti, O and N in TOV and TNV; FIG. 1F shows high-resolution TEM images of TOV and TNV exhibiting the overall morphology and the planes are labeled in the insets (scale bar=200 nm); FIG. 1G shows Raman scattering spectra showing the characteristic peaks of rutile $TiO_2$ and TiN. FIG. 1H depicts the surface of an implantable medical device (stainless steel bone fastener) having TiN nanowires formed thereon.

FIG. 2A shows cyclic voltammetry (CV) curves acquired at 100 mV s$^{-1}$ from the second cycle; FIG. 2B shows galvanostatic charging-discharging curves acquired at 0.1 mA cm$^{-2}$ from the second cycle; FIG. 2C is a discharging curve recorded in the first 1000 s after charging TO and TN to 2 V; FIG. 2D shows the total discharging capacity of the different samples charged to 2 V.

FIG. 3A shows antibacterial effects of TO, FIG. 3B shows the electrically charged TO/TN nanowires with different orientations against *E. coli*; FIG. 3C shows the antibacterial effects of TO, FIG. 3D shows electrically charged TO/TN nanowires with different orientations against *S. aureus*; FIG. 3E shows real-time viability of *E. coli* and *S. aureus* on the different (charged) samples (scale bar=50 μm); FIG. 3F shows bacterial morphology after cultivation on the different (charged) samples (scale bar=1 μm).

FIGS. 4A-4I show the biophysical antibacterial mechanism FIG. 4A shows potential maps of bacteria cultivated on different samples in an area of 5 μm×5 μm illustrating cohesion at the interface (scale bar=1 μm); FIG. 4B is a schematic diagram showing how the retract line reflects the adherence force; FIG. 4C is a retract force-distance curve of the AFM tip from the bacteria on different samples; FIG. 4D is the adhesion force between the bacteria and sample surface calculated from the non-linear part of the retract curves in FIG. 4C; FIG. 4E is the membrane stiffness calculated from the linear part of the curves in (FIG. 4C); FIG. 4F shows the simulated interface between the sample surface and bilayer at different time under different conditions; FIGS. 4G-4H are Gaussian curvature fittings of the bilayer non-voltage (4G) and voltage trajectories (4H); FIG. 4I is the compressibility $K_A$ of the bilayer after interacting with the surfaces with/without charging.

FIGS. 5A-5E show the biochemical antibacterial mechanism. FIG. 5A show dots emitting red/green fluorescence after staining the membrane by the potential kit and detected by flow cytometry with gates to exclude the debris. The bacteria in TNV are distributed in two regions due to different states of the membrane potentials; FIG. 5B is a quantitative comparison of the membrane potentials characterized as R/G ratios; FIG. 5C shows TEM images of the bacteria on the different samples (scale bar=500 nm); FIG. 5D shows fluorescent staining images of intracellular ROS of the bacteria on the different samples (scale bar=50 μm); FIG. 5E is a schematic diagram showing how bacteria are affected on the different surfaces.

FIG. 6C shows infection and inflammation state of the surrounding tissues after Gram and H&E staining, respectively (scale bar=100 μm). The infected areas are circled in red and marked with red arrows and the inflammation parts are marked with black arrows.

μm). The biophysical changes during the bacteria-material interactions indicate the bacteria-killing process. The surface topography and potential maps of the samples in a 5 μm×5 μm area are scanned by AFM using the tapping mode. The 3D surface topographical images offer information about not only the bacteria location (2D image), but also the height from the surface (brightness, FIG. 14). The bacteria distribution resembles that revealed by SEM. The bacteria density on the control and TNT is so large that the substrate can hardly be recognized. In contrast, few bacteria adhere onto the surface of TNI, TNV and +TNV and morphological disruptions are detected (black arrows). Notably, the bacteria on +TNV are mostly deformed indicating the harshest environment after charging.

Figure 15:
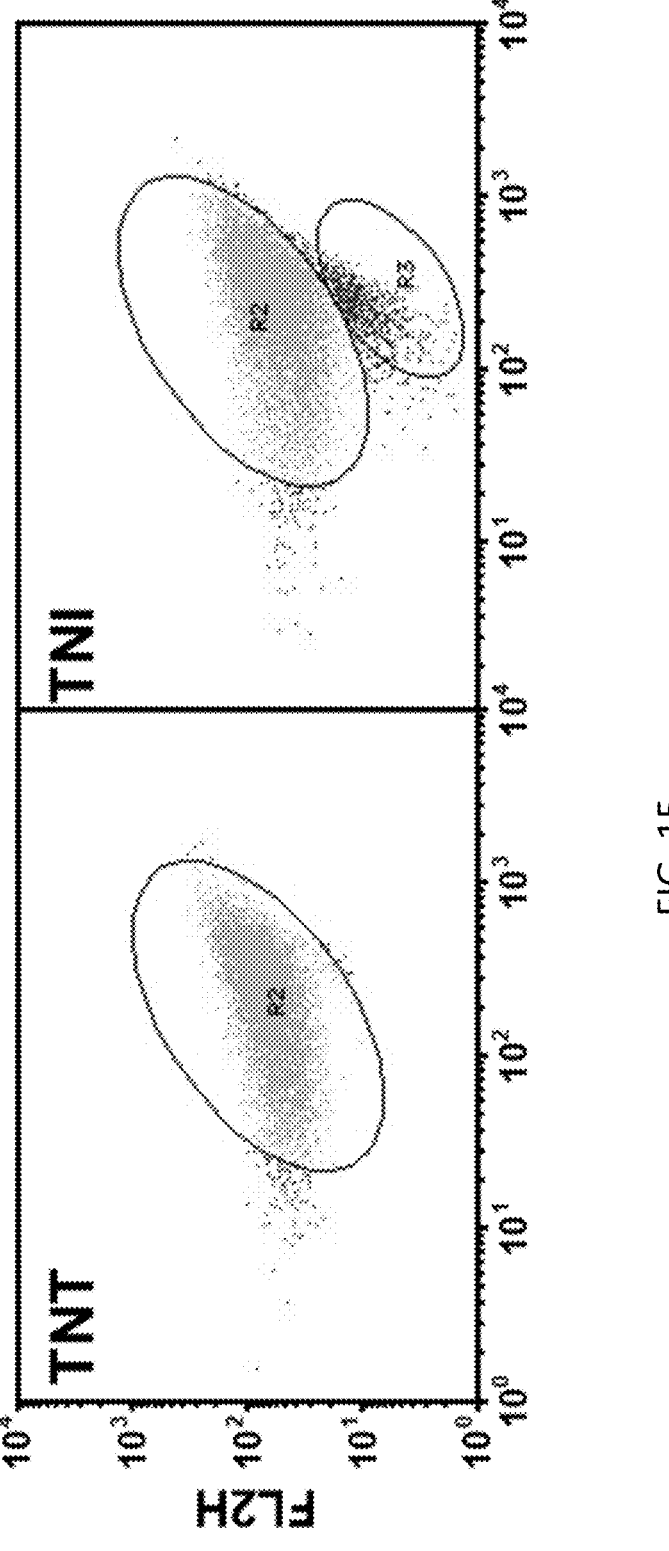

FIG. 15 shows membrane potential dots of bacteria determined by flow cytometry. As shown FIG. 15, the membrane potentials on the control and TNT are at the same level. Bacteria are distributed in two regions on TNI and TNV groups (R2 and R3). The membrane potential on R2 is similar to that of the control, but that on R3 decreases significantly, suggesting that TNI and TNV can only disrupt the bacteria upon direct contact while those in the further vicinity are not affected.

FIG. 16 shows TEM images of bacteria on TNT and TNI (scale bar=200 nm). The biochemical changes from electrochemical interactions are further examined by TEM on the sliced bacteria (FIG. 16). The bacteria experience stronger membrane disruption in the order of TNT, TNI, TNV and +TNV (black arrows).

Figure 17:
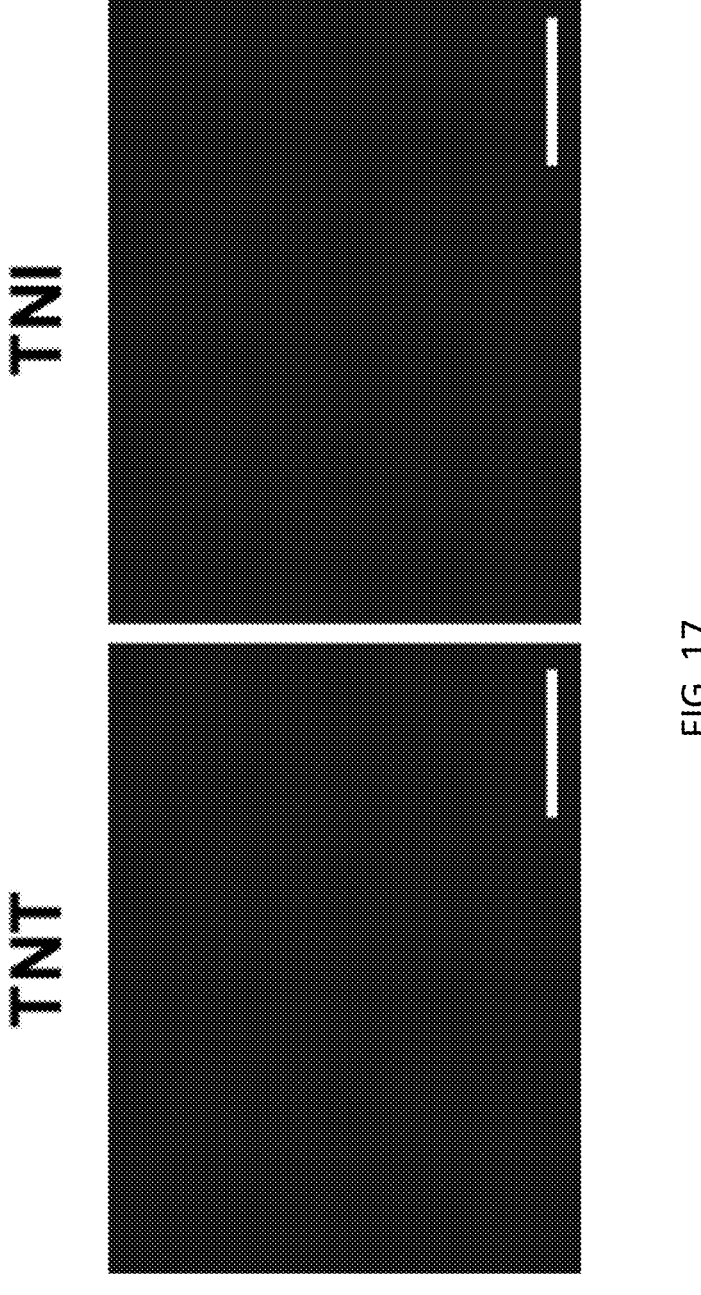

FIG. 17 shows fluorescent staining images of intracellular ROS on TNT and TNI (scale bar=50 μm). TNT, TNI, and TNV groups show similar behavior as the negative control group with no intracellular ROS spot and +TNV is similar to the positive group exhibiting significant green spots.

Figure 18A:
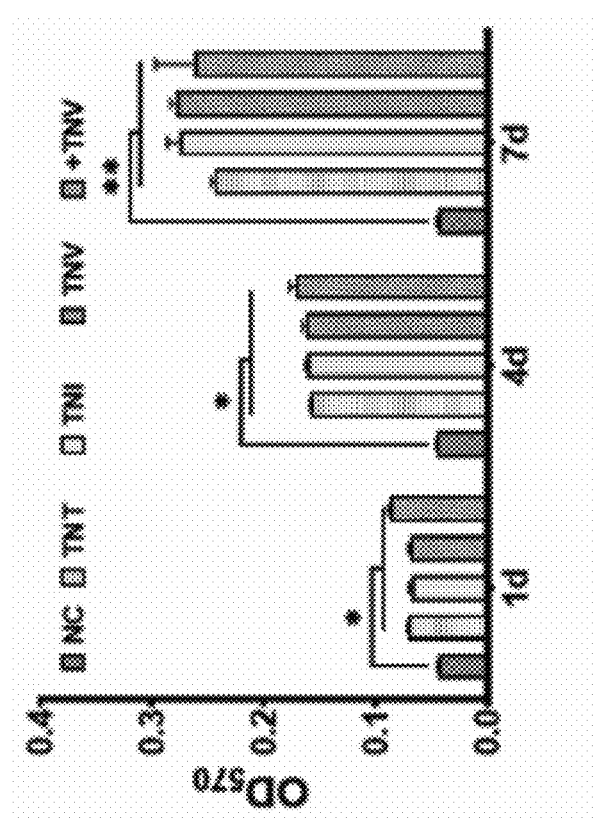
Figure 18B:
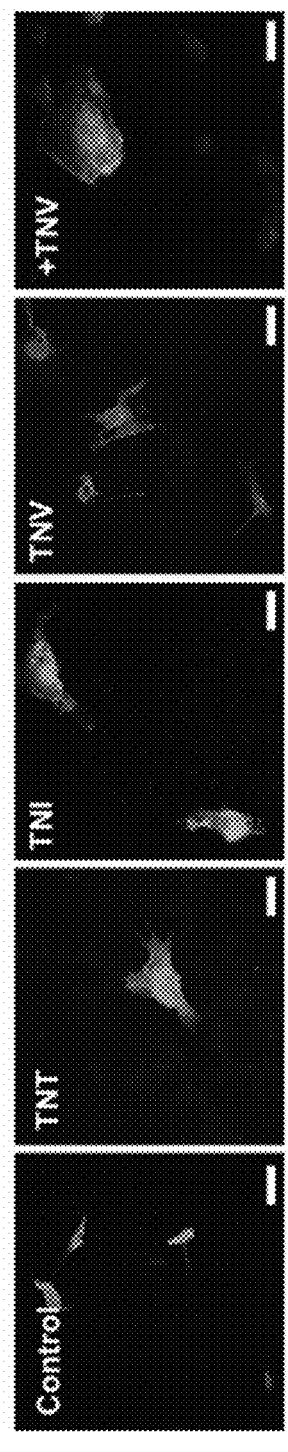
Figure 18C:
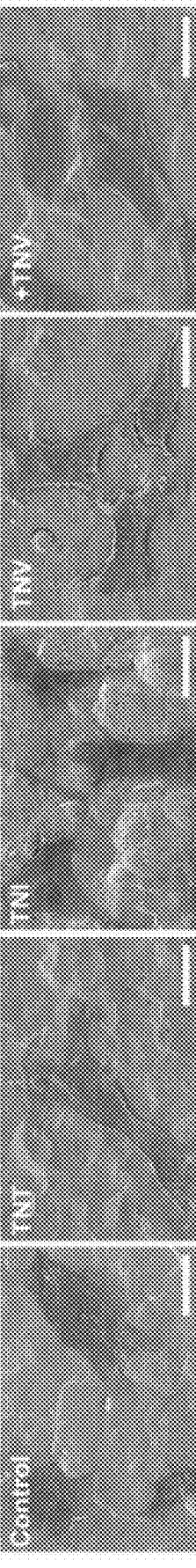

FIG. 18A-18C shows in vitro biocompatibility assessment: FIG. 18A is a quantitative determination of the cell viability at time points of 1 d, 4 d, and 7 d. * and  denote P<0.05 and P<0.01 compared to the control group, respectively; FIG. 18B shows fluorescent images depicting the cytoskeleton of the osteoblasts cultivated on the different samples for 24 h (scale bar=25 μm); FIG. 18C shows SEM images of the osteoblasts cultivated on different samples (scale bar=25 μm). +TNV fares the best in the antibacterial test and the preliminary in vitro cell experiments provide the positive signal that none of the TN samples will do harm with regard to adherence and proliferation of osteoblasts and even foster the growth of osteoblasts as indicated by MTT (18A). The cytoskeleton of the osteoblasts after cultivation for 24 h is observed after fluorescent staining (18B). The osteoblasts in the four TN groups adhere onto the substrate and proliferate well showing spreading filopodia in a larger area than the control. The magnified SEM image is consistent (18C**). Comparing the charged and uncharged groups, no significant difference is found illustrating that the nanostructure but not the positive charge, boosts the growth of osteoblasts.

DETAILED DESCRIPTION

The present invention relates to the formation of titanium nitride nanowires on medical implants; the present disclosure also quantitatively expresses the effects of physical and electrical interactions on bactericidal properties.

Turning to the drawings in detail, FIG. 1H depicts an antibacterial implantable medical device or medical material 100. An implantable medical device or medical material 10 has a surface 12. In FIG. 1H, the implantable medical device is a bone fastener, in particular, a stainless steel bone fastener. A titanium coating 20 is formed on the implantable medical device or medical material 10. Titanium nitride nanowires 30 extend from the titanium coating on the implantable medical device or medical material 10. The titanium nitride nanowires extend at a selected angle (e.g., 60 to 90 degrees) from the titanium coating configured to exert a mechanical and/or electrical force on bacteria bilayer membranes sufficient to at least partially disrupt the bacteria bilayer membranes. In some embodiments, the selected angle is between approximately 60 and approximately 90 degrees. In some other embodiments, the selected angle is approximately 90 degrees.

The implantable medical device or medical material may be selected from a wide variety of implantable devices and materials, including, but not limited to, fasteners (such as bone fasteners, intramedullary nails, bone screws, plates, rods, pins, etc.), artificial joints (hip replacements, knee replacements, shoulder replacements, etc.), bone grafts, stents, pacemakers, cochlear implants, contraceptive implants, electrical stimulators, or any other implant that can carry a titanium coating with titanium nitride nanowires formed thereon.

To form the implants, a layer of titanium is deposited on the surface of an implantable medical device of material. The technique for forming the layer of titanium is not particularly limited and may be deposited by sputtering, magnetron sputtering, evaporation, chemical vapor deposition, powder coating, or any other known coating technique. The layer of titanium is formed to a thickness of approximately 10-1000 microns.

$TiO_2$ nanowires with different densities and orientations are fabricated on titanium by a chemical dissolution-nucleation technique and the morphological changes are shown in FIG. 7. The initial acidic and oxidizing environment fosters the formation of $Ti^{4+}$ via reaction (1). Owing to stable and gradual hydrolysis of melamine, the acidity is weakened followed by nucleation of $TiO_2$, leading to gradual growth of $TiO_2$ nanowires by reactions (2) and (3).

$$Ti+4H^++2H_2O_2 \rightarrow Ti^{4+}+4H_2O \tag{1}$$

$$Ti^{4+}+4H_2O \rightarrow Ti(OH)_4+4H^+ \tag{2}$$

$$Ti(OH)_4 \rightarrow TiO_2\downarrow+H_2O \tag{3}$$

Figure 1A:
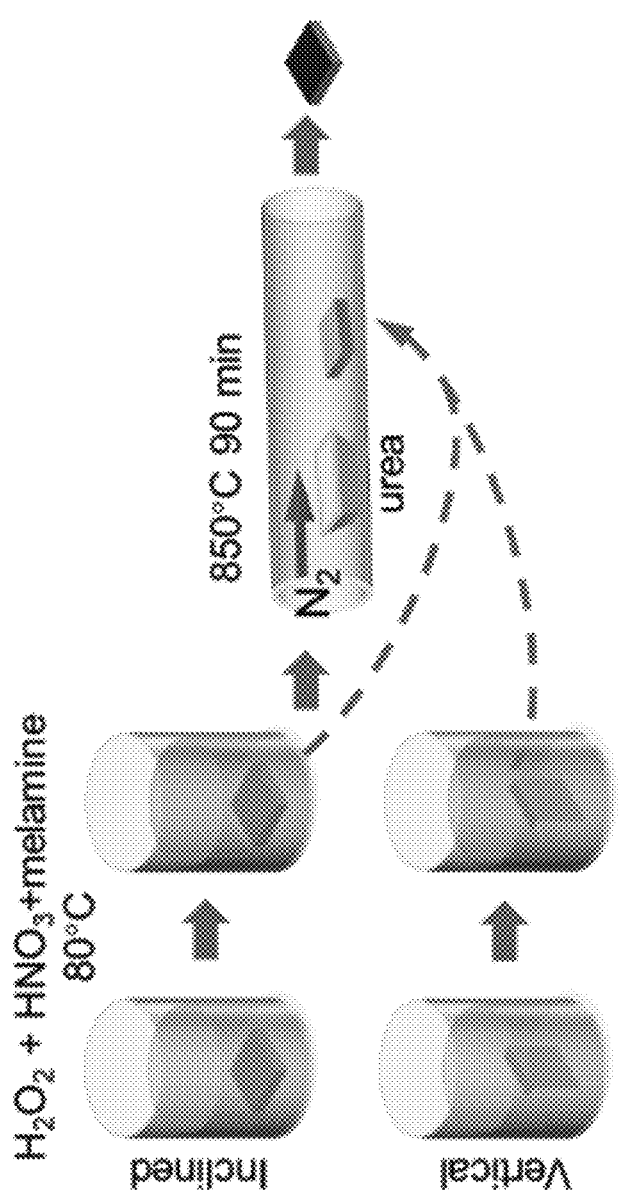
Figure 1B:
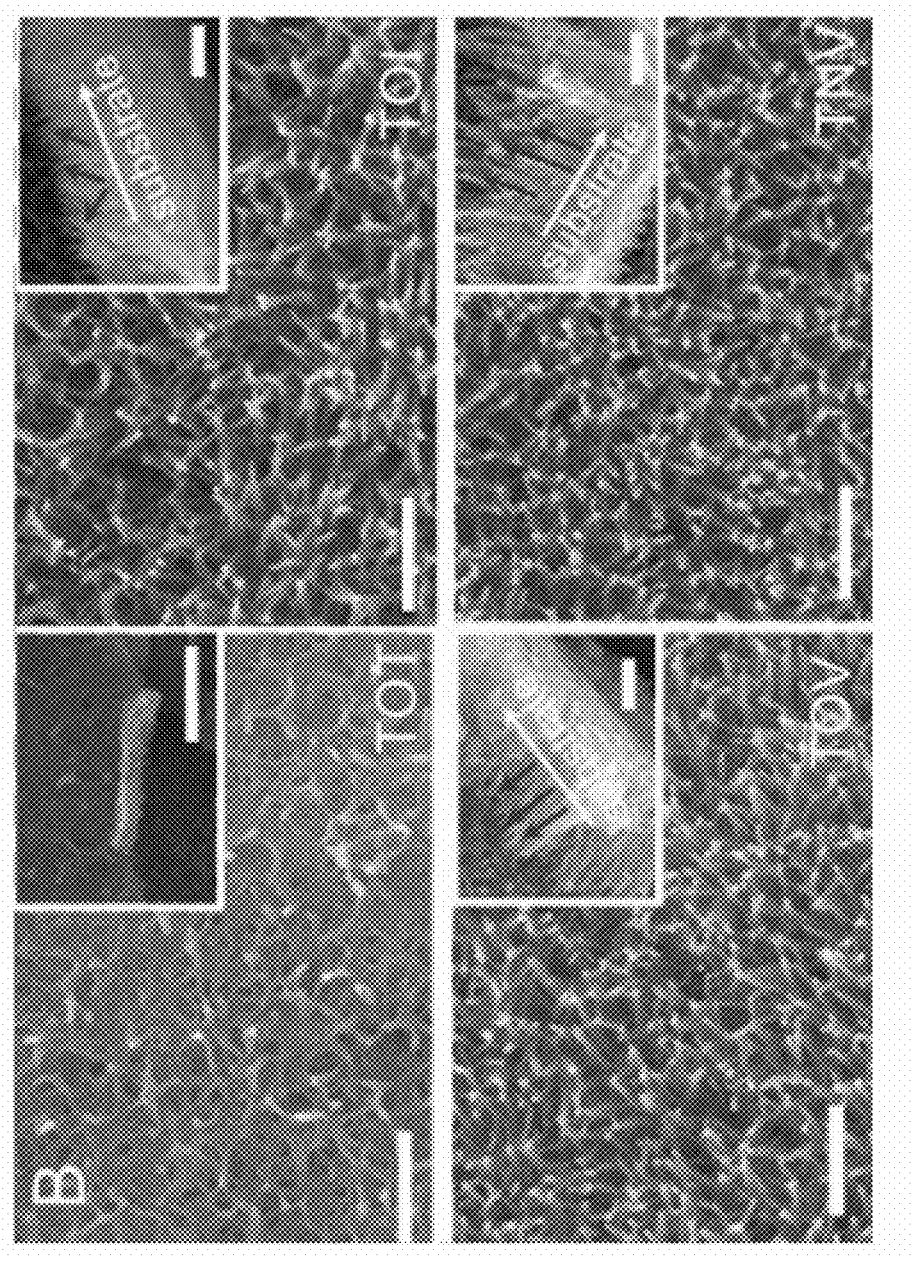

The orientation of the nanowires can be regulated by the reaction time and initial orientation of the titanium coating on the medical implant substrate (FIG. 1A). After reacting for 2 h, the nanowires are tiled (sample designated as TOT). When the reaction time is increased to 10 h, nanowires with an average diameter of 30 nm and length of 500 nm are formed and scattered on the substrate. For the samples placed horizontally and vertically in the apparatus, the nanowires grow at oblique angles of 40-50° (sample designated as TOI) and vertically at 80-90° (sample designated as TOV), respectively (red arrows in FIG. 1B).

Following formation of the $TiO_2$ nanowires, the $TiO_2$ nanowires are converted to titanium nitride (TiN) nanowires. The $TiO_2$ nanowires are exposed to a nitrogen-containing atmosphere at an elevated temperature for conversion to TiN. The nitrogen-containing atmosphere may be provided by nitrogen optionally mixed with urea. The elevated temperature may be a temperature of over 800° C., for example, 850° C.

Figure 8:
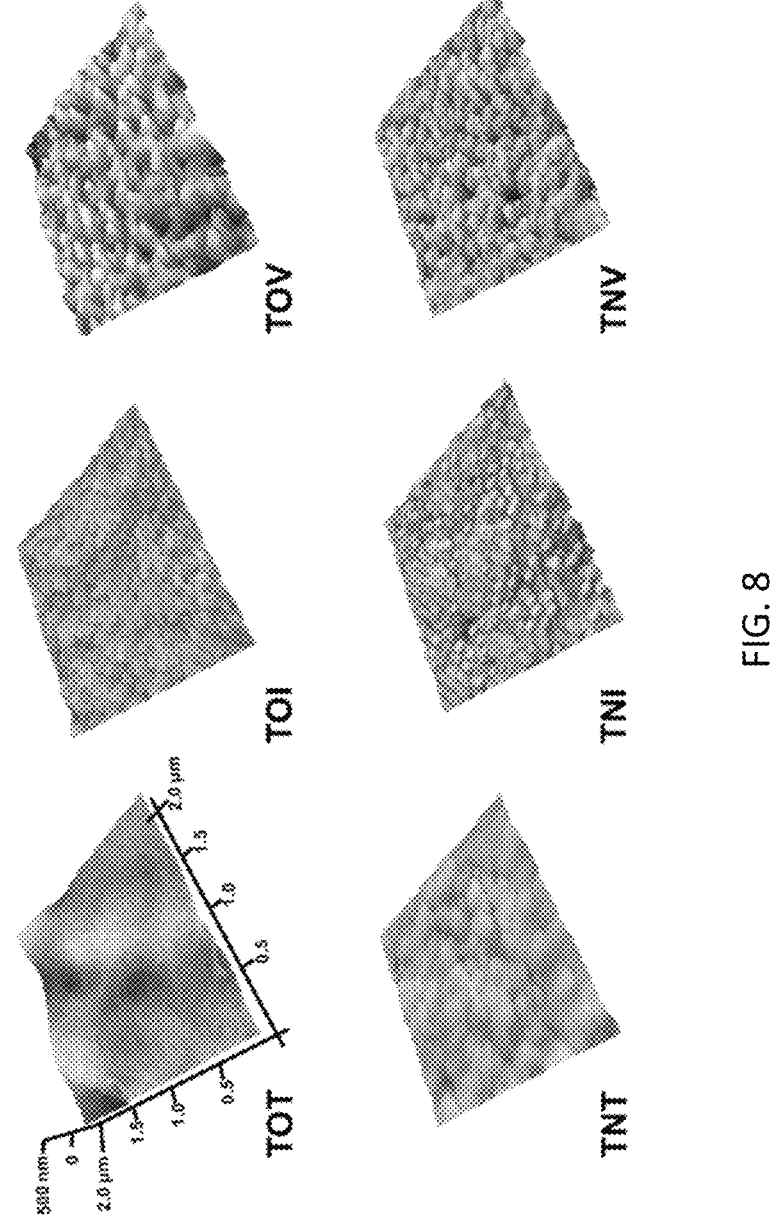
FIG. 8 shows the 3D surface morphology of the samples revealed by AFM using the tapping mode. TOT and TNT show tiled nanowires on the substrate. The nanowires on TOI and TNI grow obliquely at an angle (40°-60°) and those on TOV and TNV are almost perpendicular to the substrate.

The $TiO_2$ reacts with nitrogen to form TN, improving the capacitance, while the morphology of the nanowires is maintained (samples designated as TNT, TNI, and TNV, respectively) so that both mechanical and electrical stress can be applied to adhered bacteria on the medical implant. The morphologies of the samples are confirmed by atomic force microscopy (AFM), as seen in FIG. 8. While TNT shows tiled nanowires on the titanium layer, the nanowires on TNI grow at an angle and those on TNV are perpendicular to the titanium substrate. The different orientations are expected to exert different shear forces on adhered bacteria to cause variable destructive effects.

Figure 1C:
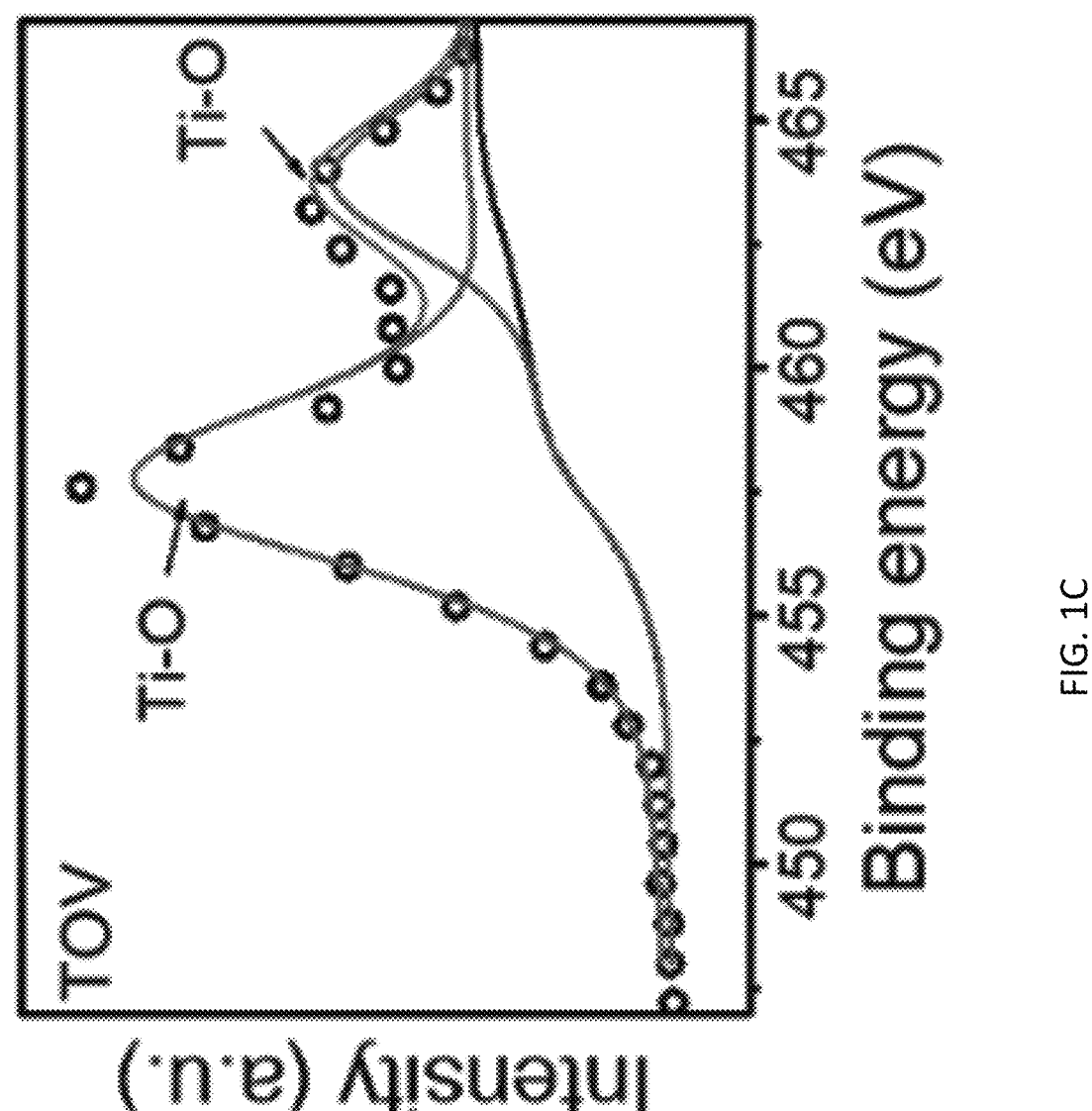
Figure 1D:
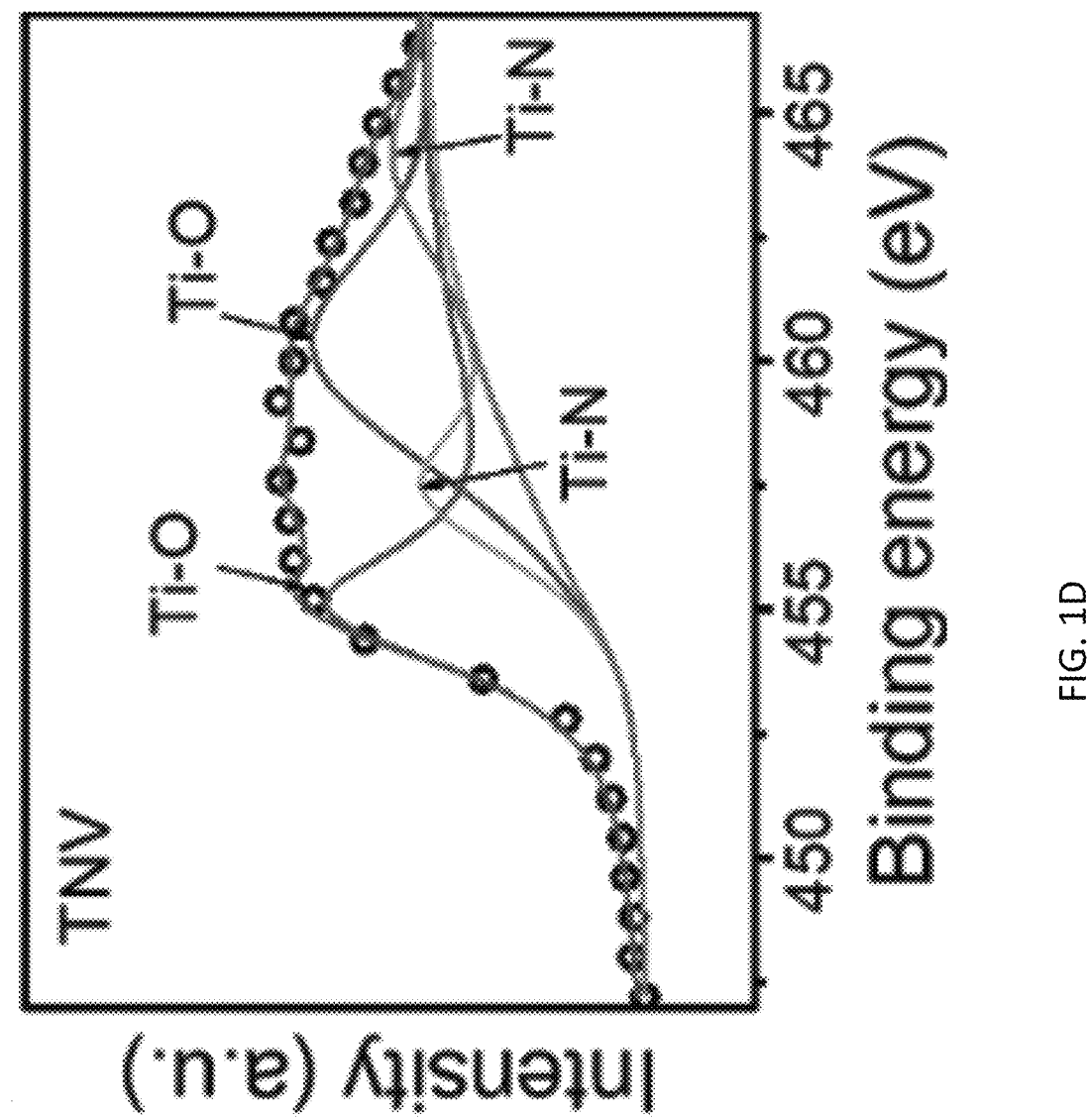
Figure 1E:
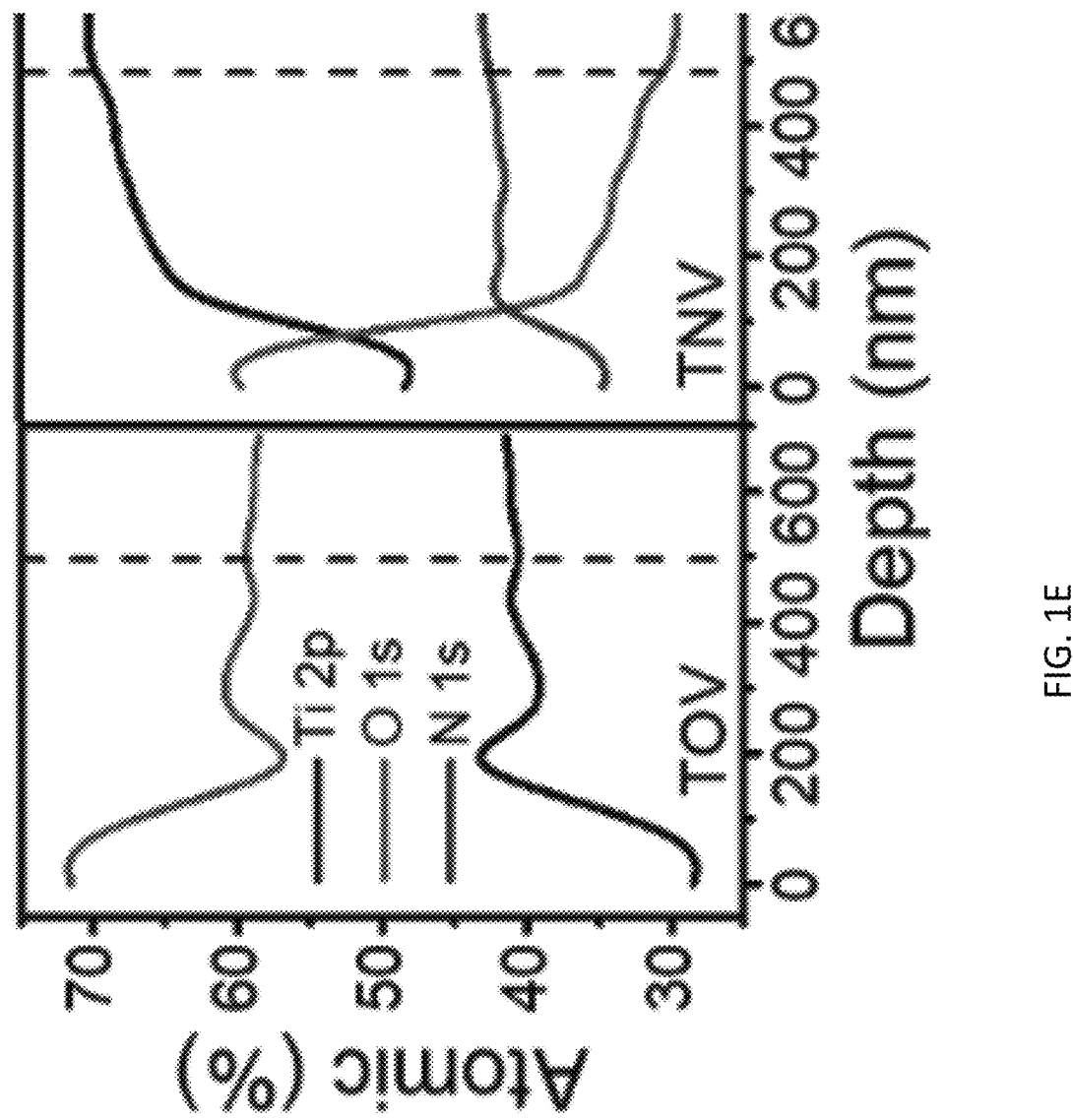
Figure 1F:
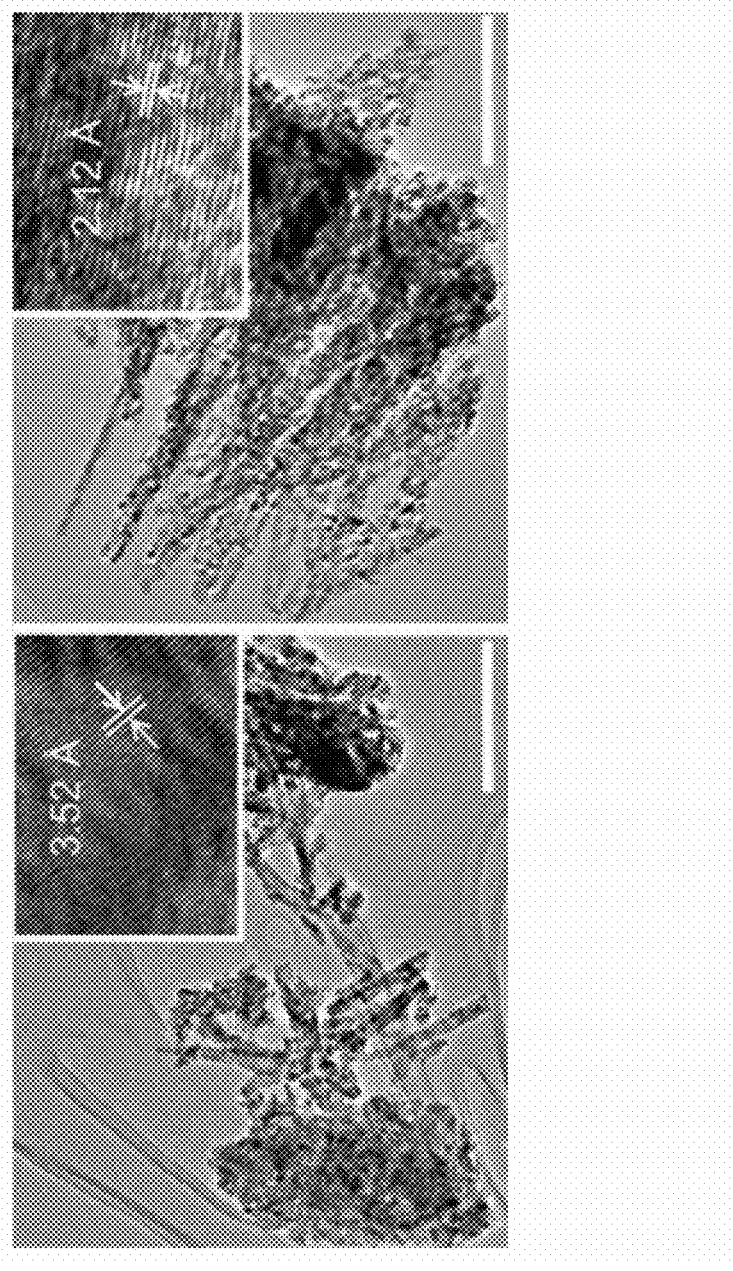
Figure 1G:
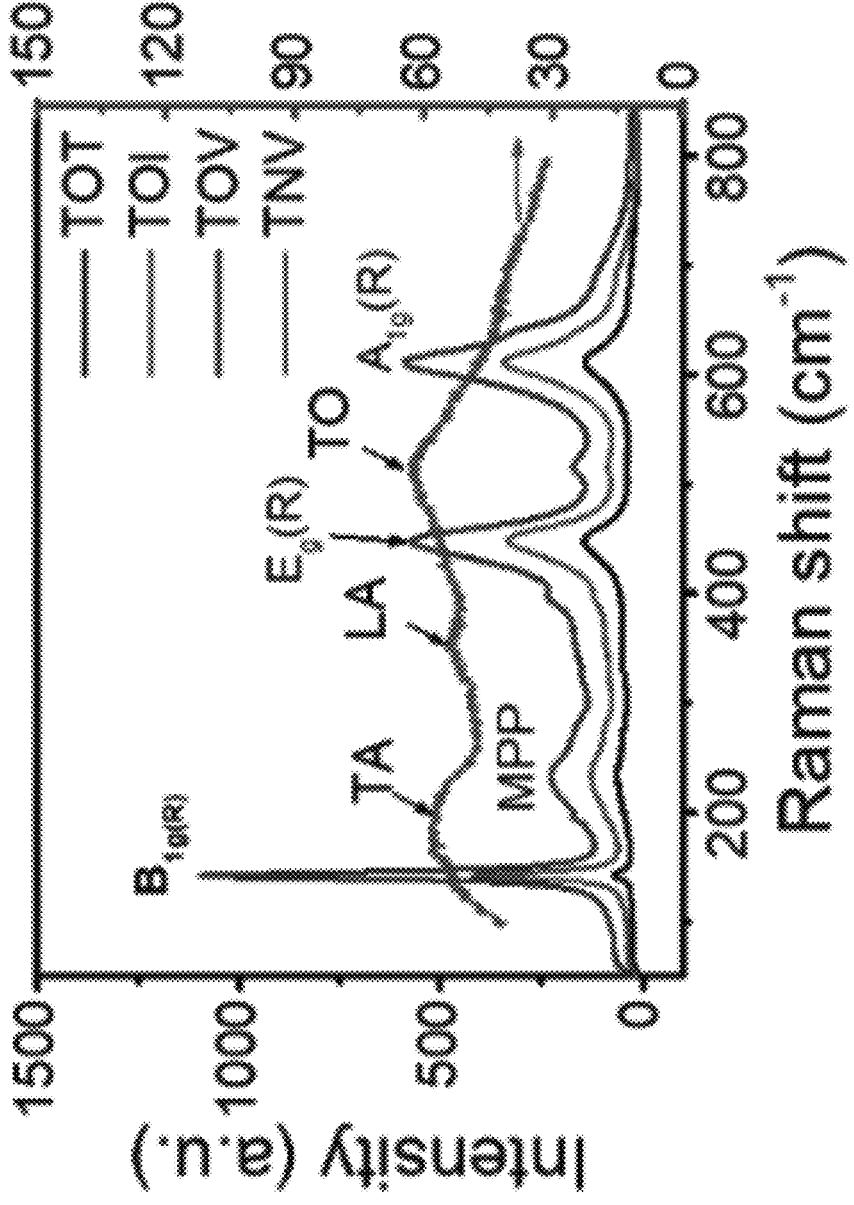
Figure 9:
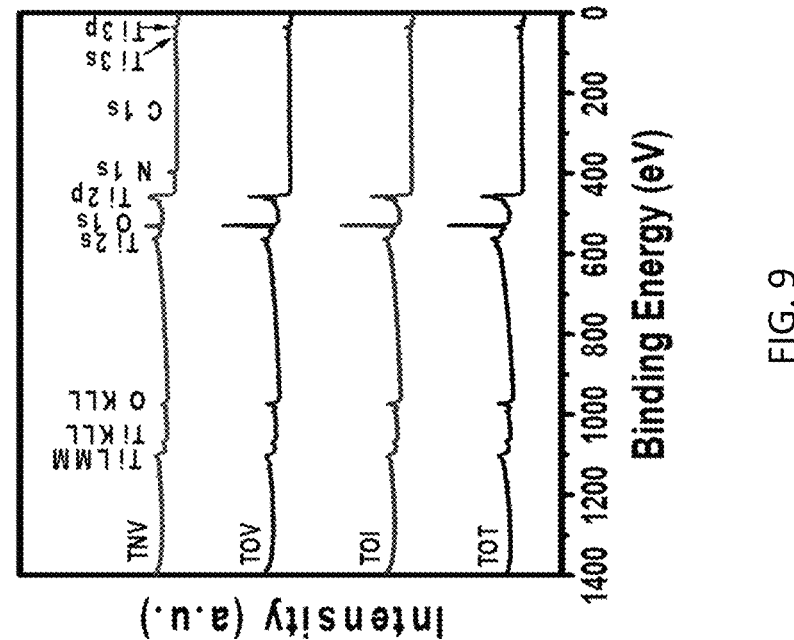
FIG. 9 is the survey XPS spectra of the samples disclosing Ti—O in TOT, TOI and TOV as well as transformation from T-O to T-N on TNV.
Figure 10:
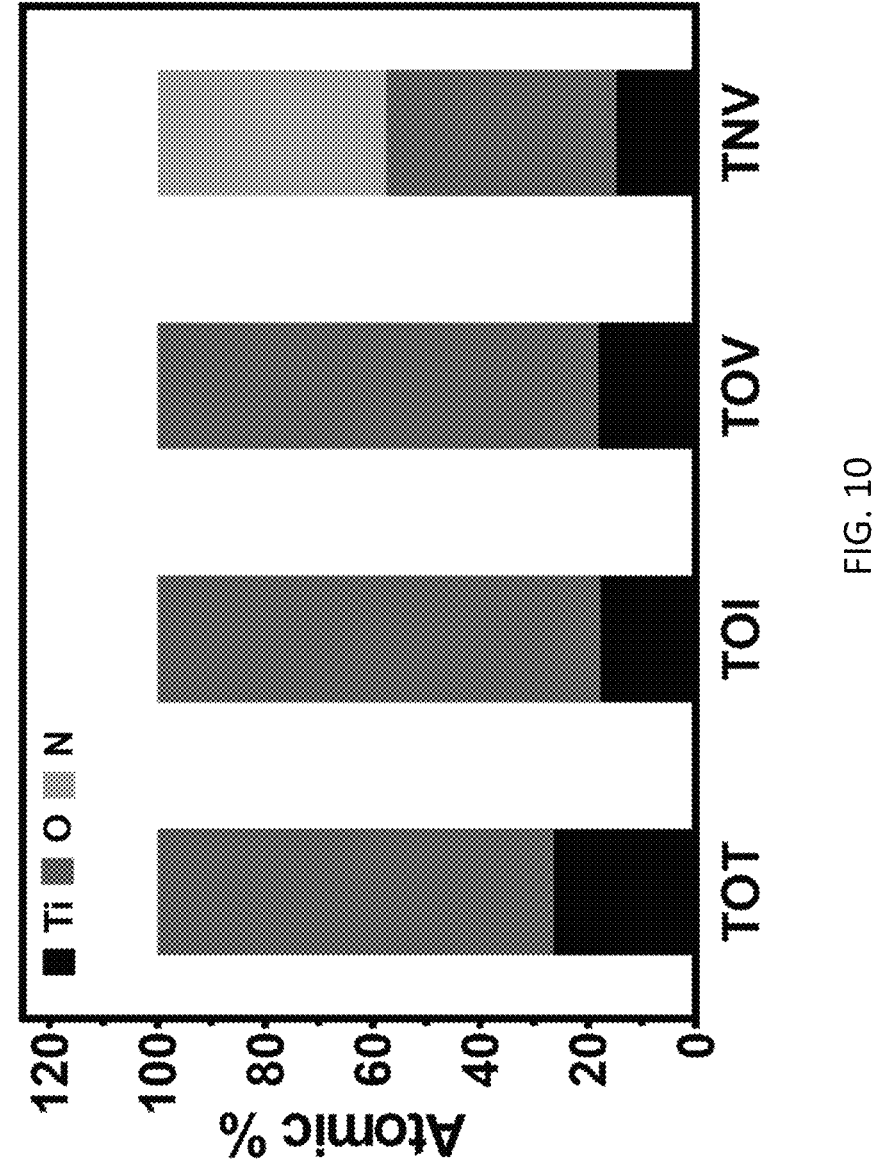
FIG. 10 is a semi-quantitative analysis of Ti, O, and N by EDS. The spectrum of TO is dominated by Ti and O, whereas after addition of N, TNV is doped with nitrogen.
Figure 11:
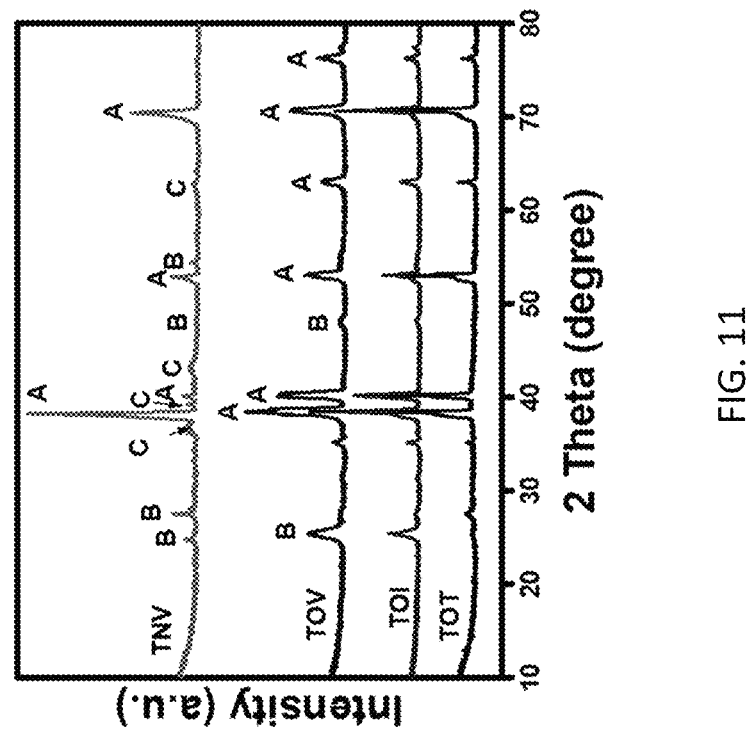
FIG. 11 shows XRD patterns of the different samples showing peaks of A-Ti, B-rutile $TiO_2$, and C—TiN.

The Ti—O bond on TOT, TOI, and TOV and transformation from T—O to T—N (TNV) are analyzed by the XPS survey spectrum (FIG. 9), high-resolution spectra of Ti 2p (FIGS. 1C and 1D), and semi-quantitative EDS spectra (FIG. 10). The depth profiles of TOV show that the O: Ti ratio is roughly 2:1 indicating the formation of $TiO_2$ nanowires with a length of 500 nm (FIG. 1E). The difference between TOV and TNV lies in the nitrogen content but there is no morphological difference. The [101] plane of $TiO_2$ and plane of TiN are observed from the high-resolution TEM images (FIG. 1F). Rutile $TiO_2$ is the dominant phase in TO as indicated by the Raman scattering peaks at 144, 394, 514 and 634 $cm^{-1}$ and the Raman peaks of TNV at 210-230, 310-330, and 540-560 $cm^{-1}$ correspond to the transverse acoustic, longitudinal acoustic, and transverse optical modes of TiN nanocrystals (FIG. 1G) consistent with XRD (FIG. 11). These results confirm the formation of TO and TN with the predesigned morphological, crystalline, and chemical properties.

Figure 2A:
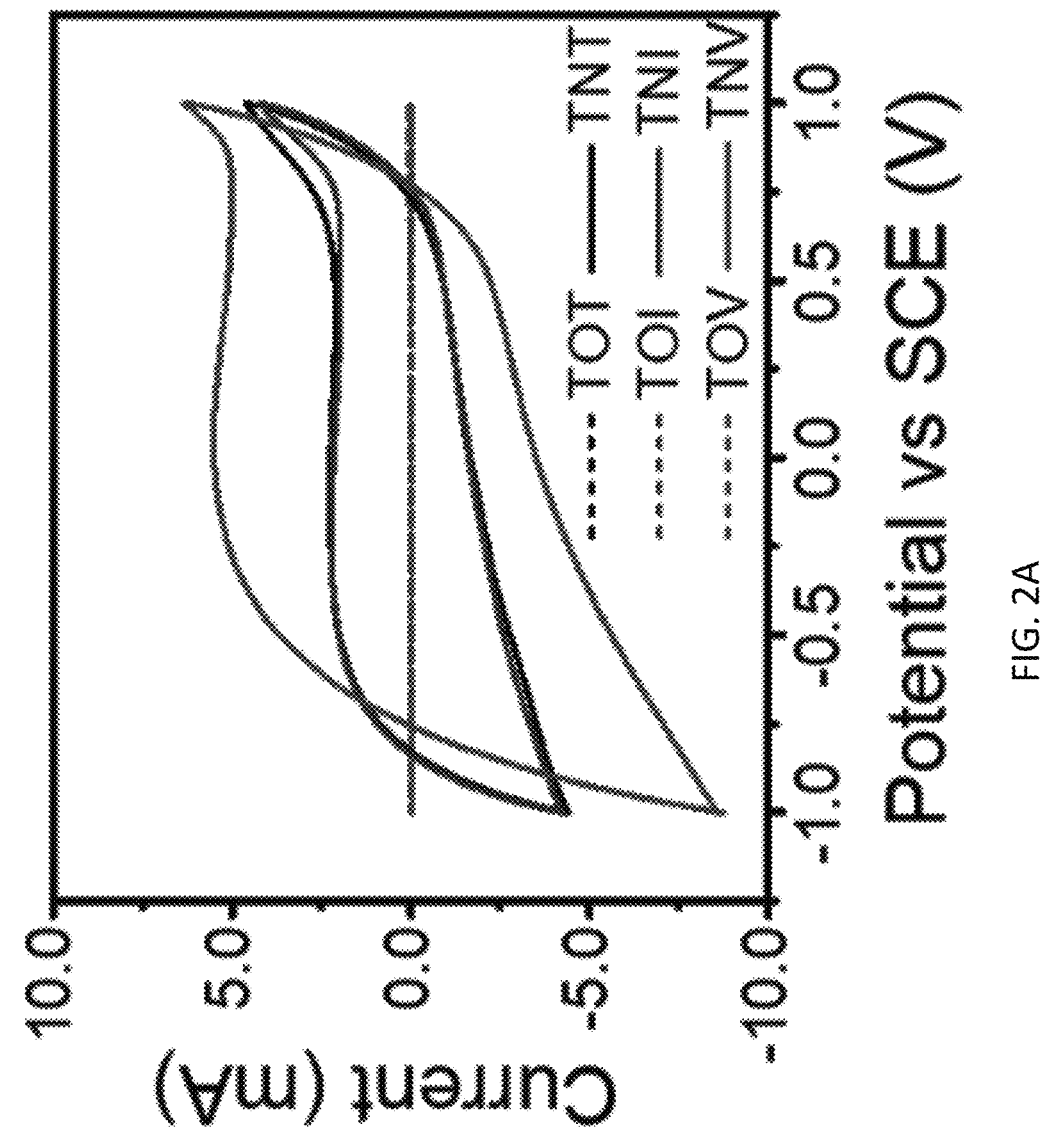
FIGS. 2A-2D show electrochemical properties of TO and TN.
Figure 2B:
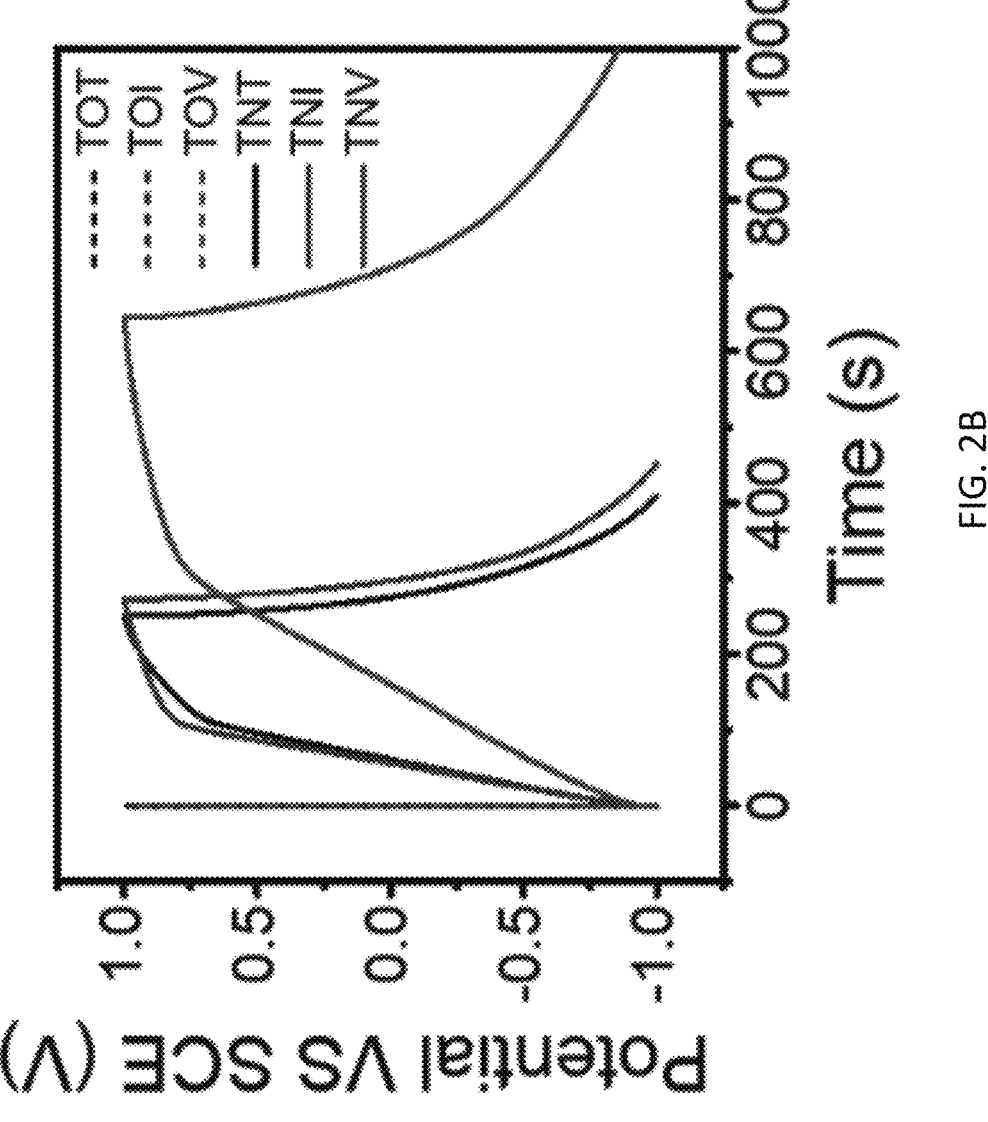
Figure 2C:
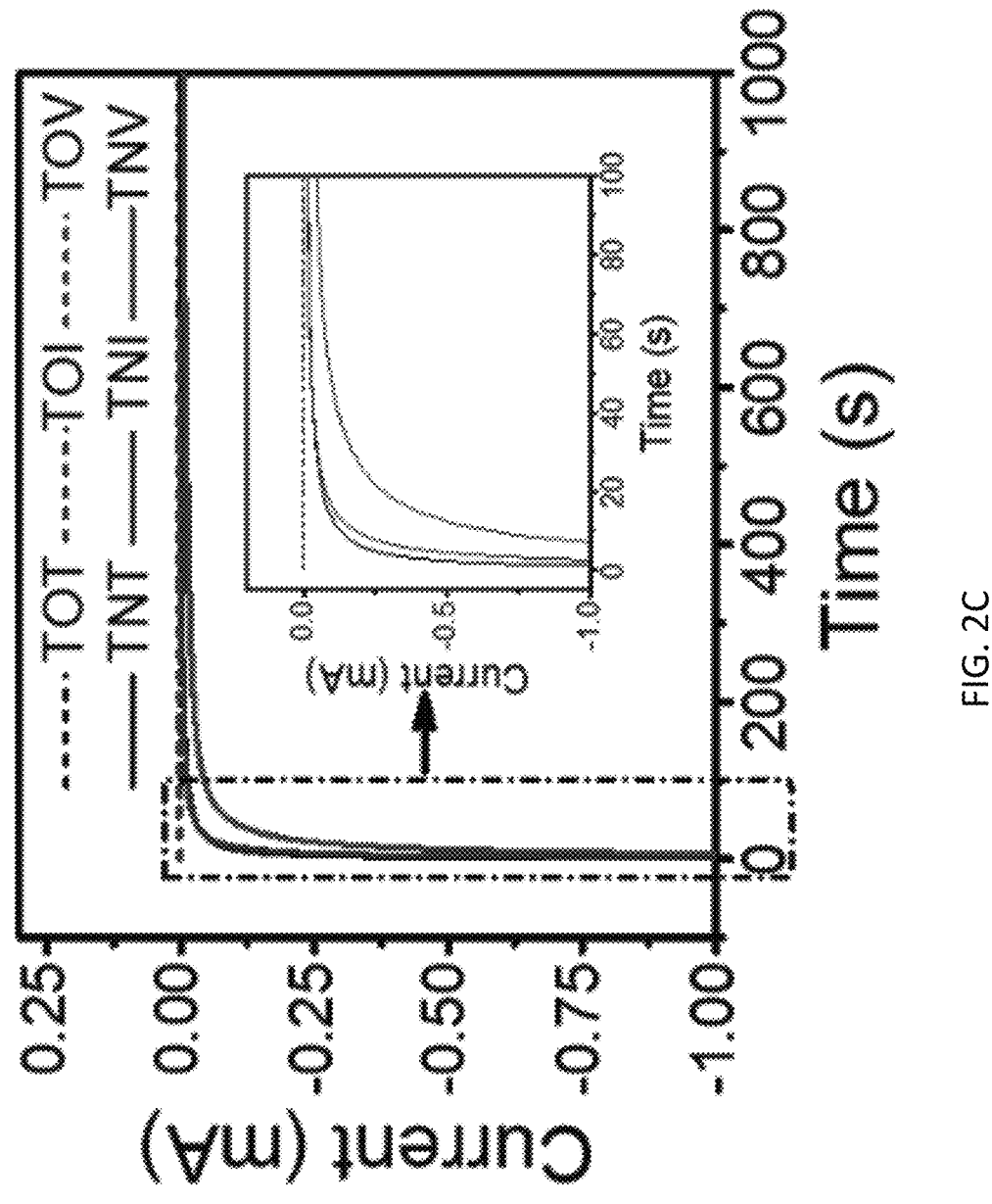
Figure 2D:
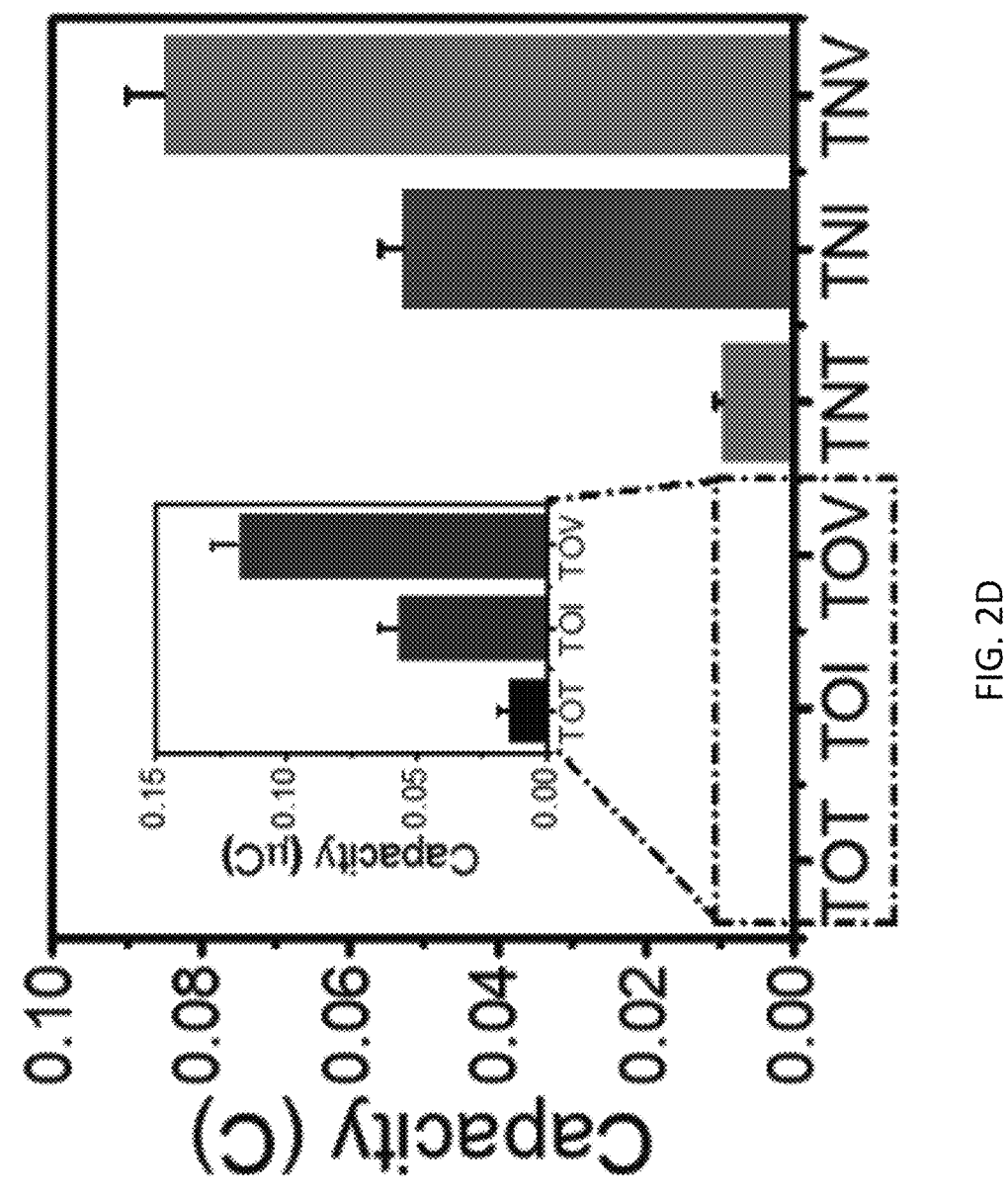
Figures 12A, 12B:
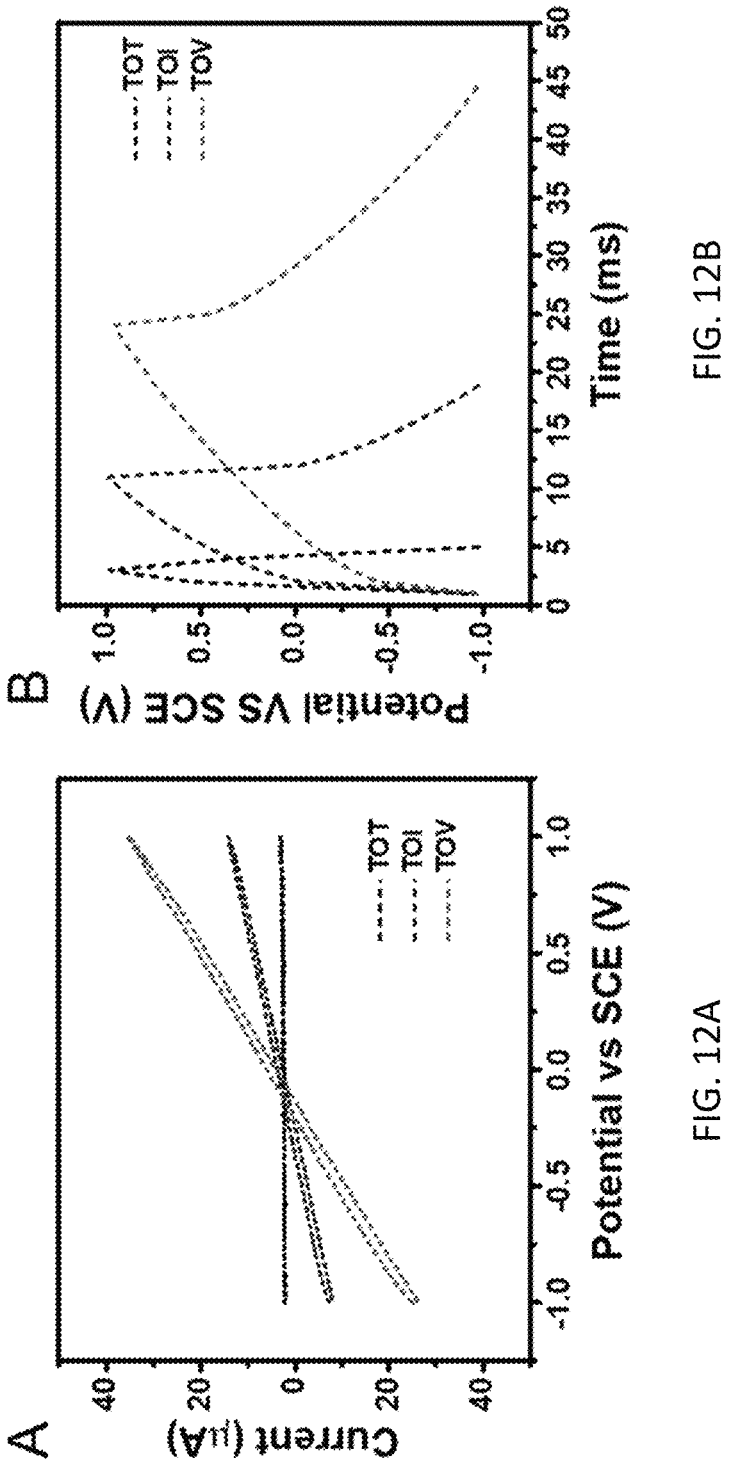
FIGS. 12A-12B show electrochemical properties of TO: (12A) Cyclic voltammetry (CV) curves acquired at 100 mV s$^{-1}$ from the second cycle; (12B) Galvanostatic charging-discharging curves acquired at 0.1 mA cm$^{-2}$ from the second cycle. As shown in fig. S6A, TOT, TOI, and TOV do not show an obvious electrochemical double-layer (EDL). TN performs better than TO with TNV showing the longest charging and discharging time (FIG. 2B and FIG. 12B).

As electrical interactions play an important role in the antibacterial action of the coating, the electrochemical properties of the samples are determined. The capacitive properties are evaluated using a three-electrode configuration in an electrolyte composed of Luria broth (LB). The cyclic voltammetry (CV) curves acquired from TO and TN at a scanning rate of 100 mV $s^{-1}$ are presented in FIG. 2A and FIG. 6A. TOT, TOI, and TOV do not show an obvious electrochemical double-layer (EDL) (FIG. 12A) as opposed to the typical EDL capacitive characteristics observed from TNT, TNI and TNV. Furthermore, the CV profile of TNV shows the maximum area and largest capacitance. The galvanostatic charging-discharging (GCD) plots obtained at 0.1 mA $cm^{-2}$ display a trend similar to CV with TN performing better than TO and TNV showing the longest charging and discharging time (FIG. 2B and FIG. 12B). The discharging curves of the fully charged samples are displayed in FIG. 2C. While TO shows a flat line overlapping the X-axis, TN discharges a high current in the early stage and the current decreases gradually. TNV discharges 0.08 C which is several times larger than that of TNI and TNT and orders of magnitude larger than that of TO (FIG. 2D). The electrochemical characteristics depend on the orientation and composition of the nanowires. The smaller redox potential after N doping is more than enough to account for the substantial capacitance leap. The sparse tiled nanowires on TNT do not favor electron transfer, whereas improvement is observed from the inclined nanowires on TNI. However, compared to the randomly distributed nanowires on TNI, the vertically aligned nanowires on TNV with a smaller aspect ratio enhances electron transfer with a larger energy storage density. The charged TNV can transfer more electrons to bacteria upon contact to boost the antibacterial efficiency, which will be verified in the following sections.

Bactericidal Properties

Figure 3A:
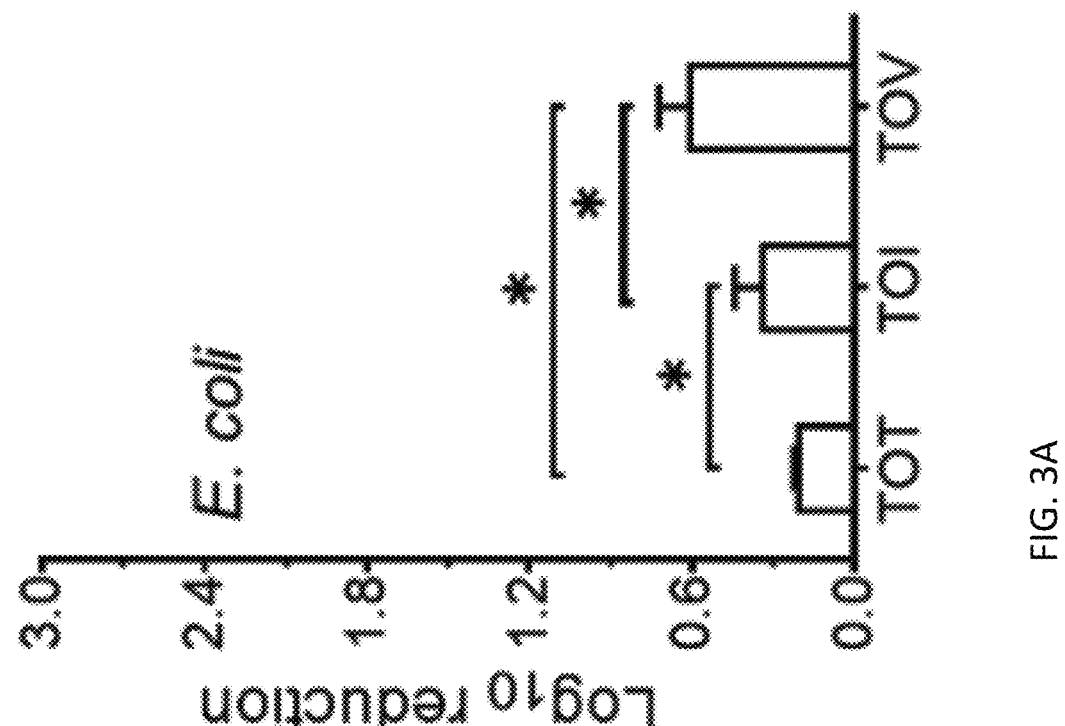
FIGS. 3A-3F show the antibacterial properties of the different samples under different conditions.
Figure 3B:
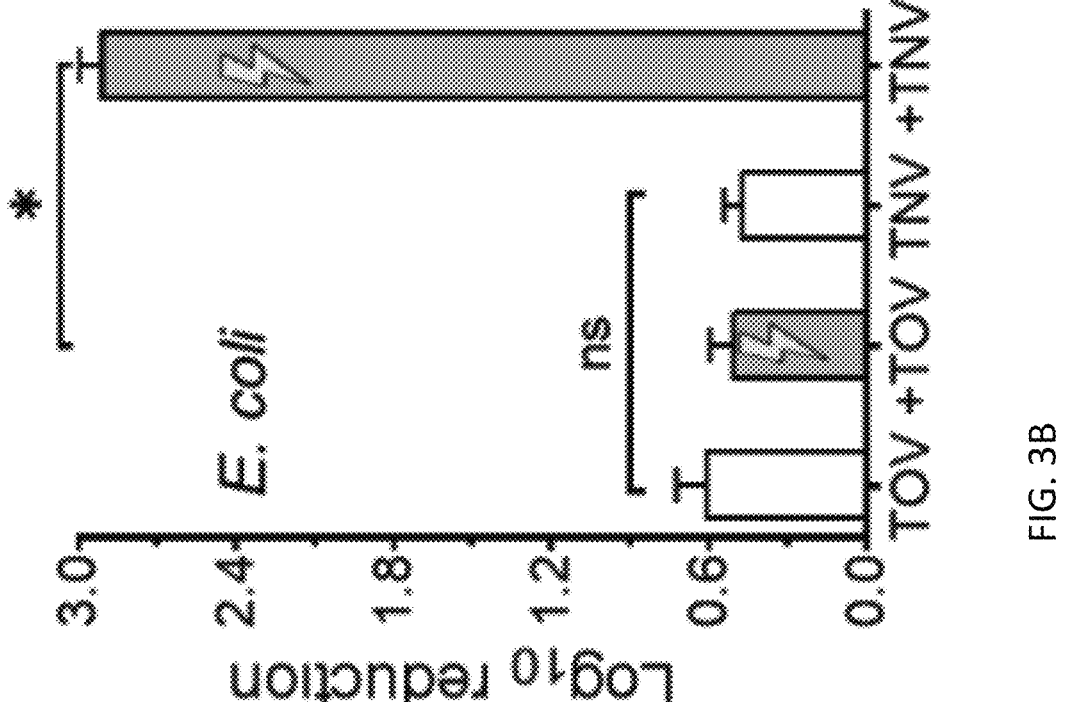
Figure 3C:
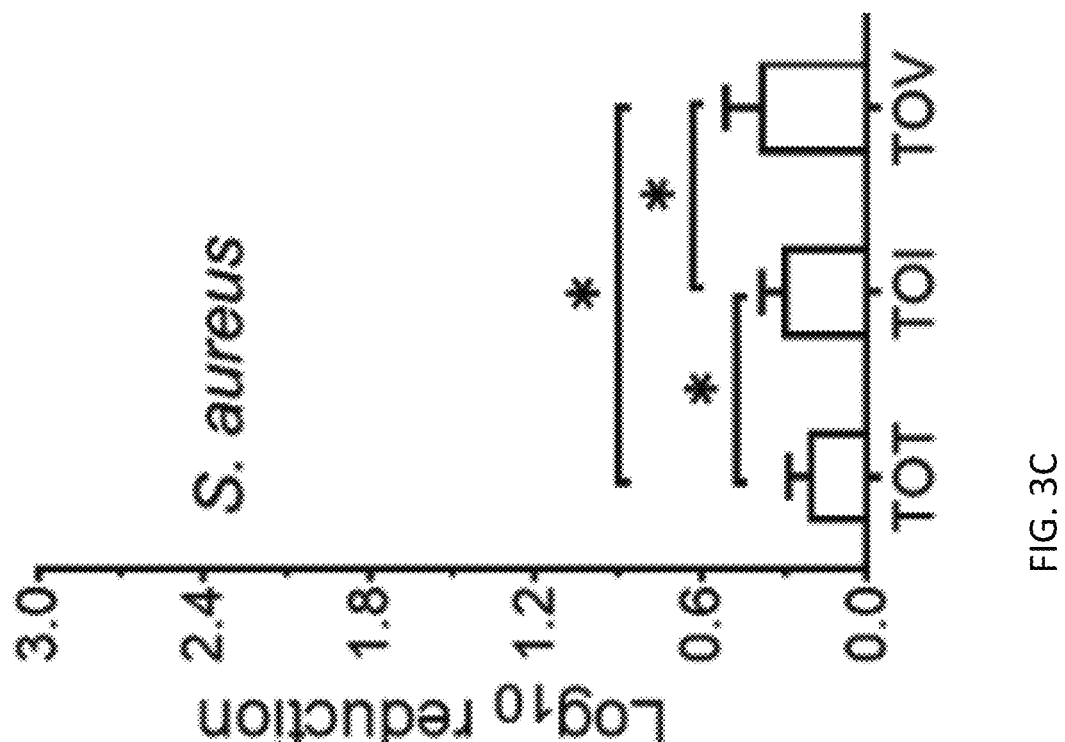
Figure 3D:
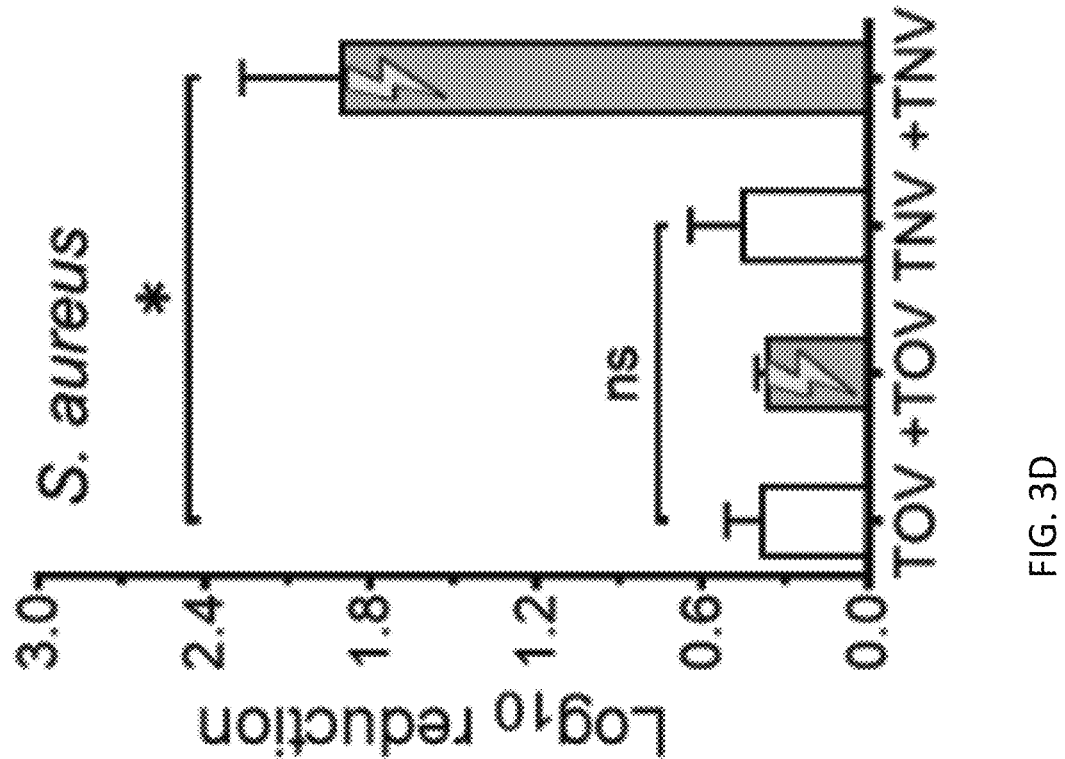

The samples with different nanostructures are subjected to bactericidal tests in which both the mechanical and electrical interactions between bacteria and the titanium nitride nanowire surface are taken into consideration. The nanowires with different orientations kill bacteria differently. After cultivation for 6 h, 40% of the bacteria on TOT are killed (0.21 log reduction), whereas the inclined nanowires on TOI can eliminate 55% of the bacteria (0.35 log reduction, FIG. 3A). In comparison, the vertical nanowires on TOV kill 75% of the bacteria (0.62 log reduction), which is the same as TNV despite the different compositions (FIG. 3B). As aforementioned, an antibacterial efficacy of 75% is unsatisfactory because a substantial number of bacteria can reform after a few hours. In this respect, charged TNV (+TNV), which may be prepared through charging with an external DC power supply, exhibits an antibacterial ability of 99.9% against *E. coli* (3 log reduction, FIG. 3B). The insignificant antibacterial effects of electrically charged TOV (+TOV) indicate that capacitance plays a significant role in the antibacterial process. A similar tendency is observed from TOV against Gram-positive bacteria *S. aureus*. TOV and TNV with vertical nanowires fare the best (~60%, 0.39 log reduction) among the uncharged samples, while +TNV after charging shows an antibacterial rate of more than 99% (2 log reduction, FIGS. 3C and 3D). The above results indicate that while doubled antibacterial ability can be achieved by adjusting the orientation of nanowires, a strikingly 5 times' promotion is further accomplished by taking advantage of the capacitance. The greatly increased antibacterial ability is associated with both mechanical and electrical interactions at the interface.

Figure 3E:
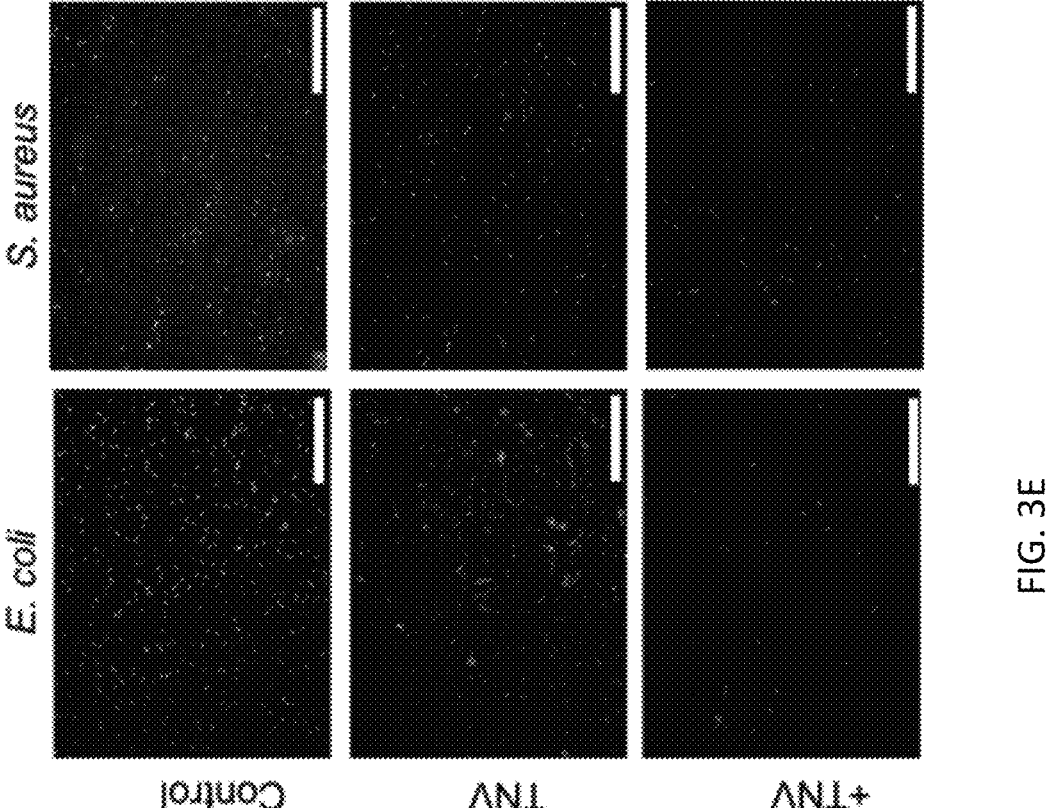

The real-time bacterial viability is evaluated by live/dead staining (FIG. 3E). Both gram-positive and gram-negative bacteria can grow, proliferate, and maintain the active viability on the titanium substrate (control). TNV provides a tougher environment with many of the bacteria showing red fluorescence, but there are still dots emitting green fluorescence as a result of bacterial reduction of less than 0.6 log. In contrast, +TNV reveals widespread red fluorescence and reduced bacteria intensity in line with the CFU counting results in FIGS. 3A-3D.

Figure 3F:
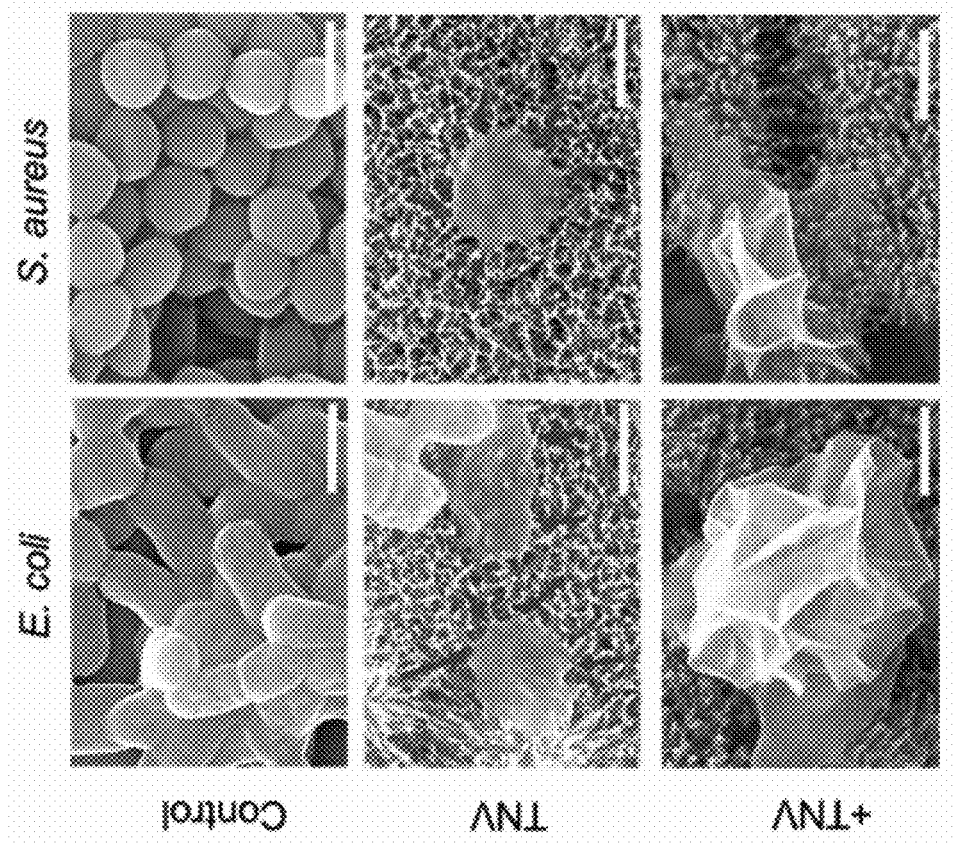
Figure 13:
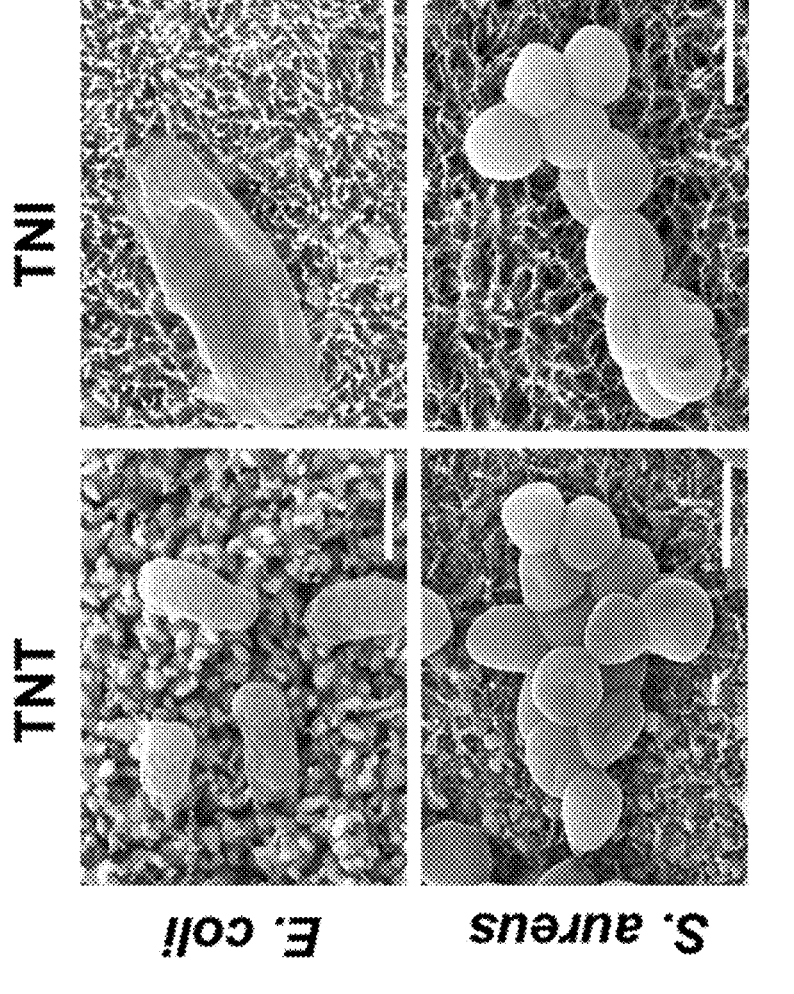
FIG. 13 is the morphology of attached *E. coli* and *S. aureus* on TNT and TNI after treatment (scale bar=1 μm). The sparsely distributed and tiled nanowires on TNT hinder proliferation of bacteria and some of them are slightly shriveled. The protruding nanowires on TNI lead to the partial membrane collapse.

As described above, bacteria are killed by the combination of mechanical and electrical interaction thus an intuitive phenomenon should be the bacterial morphological change. As shown in FIG. 3F and FIG. 13, the titanium substrate as the control is covered by a large density of *E. coli*, which maintains the typical rod shape with a length of 2 μm and diameter of 0.5 μm. The tiled nanowires on TNT hinder proliferation of bacteria and some of them are slightly shriveled. The inclined nanowires on TNI cause the bacterial membrane to collapse and the vertical nanowires on TNV flatten the whole cell (red arrows in FIG. 3F). Electrical charges further cause severe distortion so that the original rod-like morphology can no longer be recognized. *S. aureus* exhibit a similar morphological change trend, that is, a smooth spherical shape on titanium, lumpier and craggier membrane on TNT and TNV, and obvious disruption on +TNV. The morphological change illustrates that progressive stress is exerted on the bacteria in the order of TNT<TNI<TNV<+TNV. For the bacteria on +TNV, the potential difference between the positively charged TNV and negatively charged bacteria membrane enhances the electrostatic attraction and therefore, the membrane adheres more tightly to the surface with vertical nanowires and consequently, larger surface tension is exerted onto the bacteria. Besides, the potential difference may also disrupt the equilibrium of electrons in the respiration chain. These biomechanical and electrical interactions work in concert to enhance the antibacterial properties.

Biophysical Antibacterial Mechanism

Figure 4A:
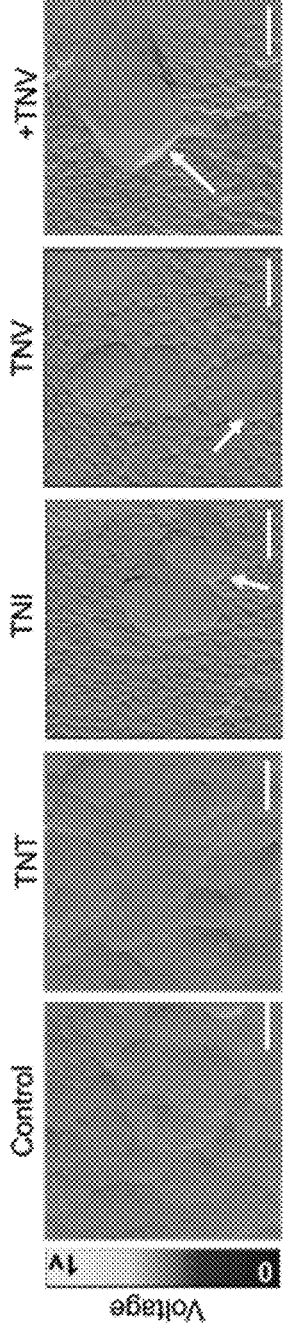
Figure 14:
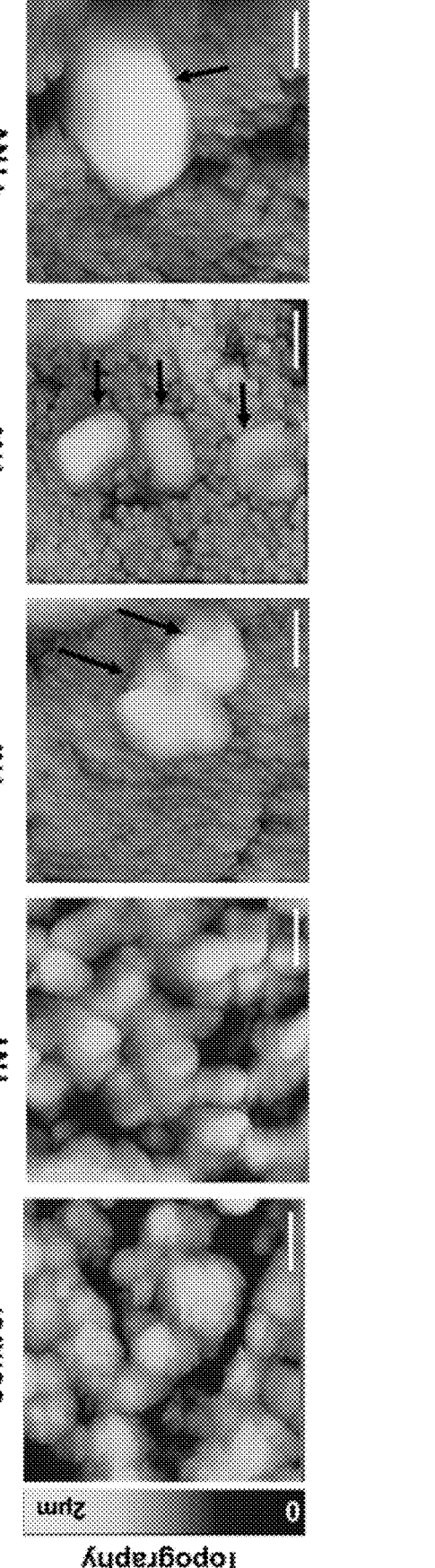
FIG. 14 shows topographical maps of bacteria cultivated on different samples in an area of 5 μm×5 μm (scale bar=1

1. Visual Images Providing Qualitative Information about the Topography and Adhesion Force The biophysical changes during the bacteria-materials interactions are studied to understand the bacteria-killing process. The surface topography and potential maps of the samples are acquired from a 5 μm×5 μm area by AFM using the tapping mode as shown in FIG. 4A and FIG. 14. The 3D surface topographical images impart information about the bacteria location (2D image) as well as height from the surface (brightness, FIG. 14). The distribution of bacteria is similar to that disclosed by SEM. The bacteria density on the control and TNT is so large that the substrate can hardly be recognized. In contrast, fewer bacteria adhere onto the surface of TNI, TNV, and +TNV and morphological disruptions are detected (black arrows in FIG. 14). The bacteria on +TNV are deformed the most severely, indicative of the harshest environment after charging. The brightness in the potential maps reflects the adhesion force (FIG. 4A). Bright edges are detected from TNI and TNV and the brightest points emerge from +TNV indicating the largest adhesion force (white arrows in FIG. 4A).

2. Quantitative Analysis of the Adhesion Force and Membrane Stiffness

Figure 4B:
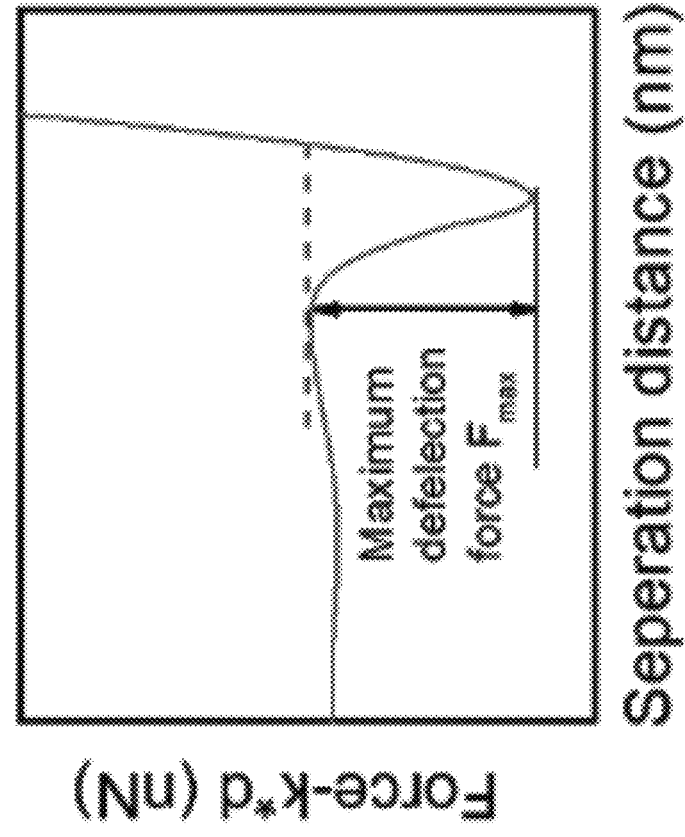
Figure 4C:
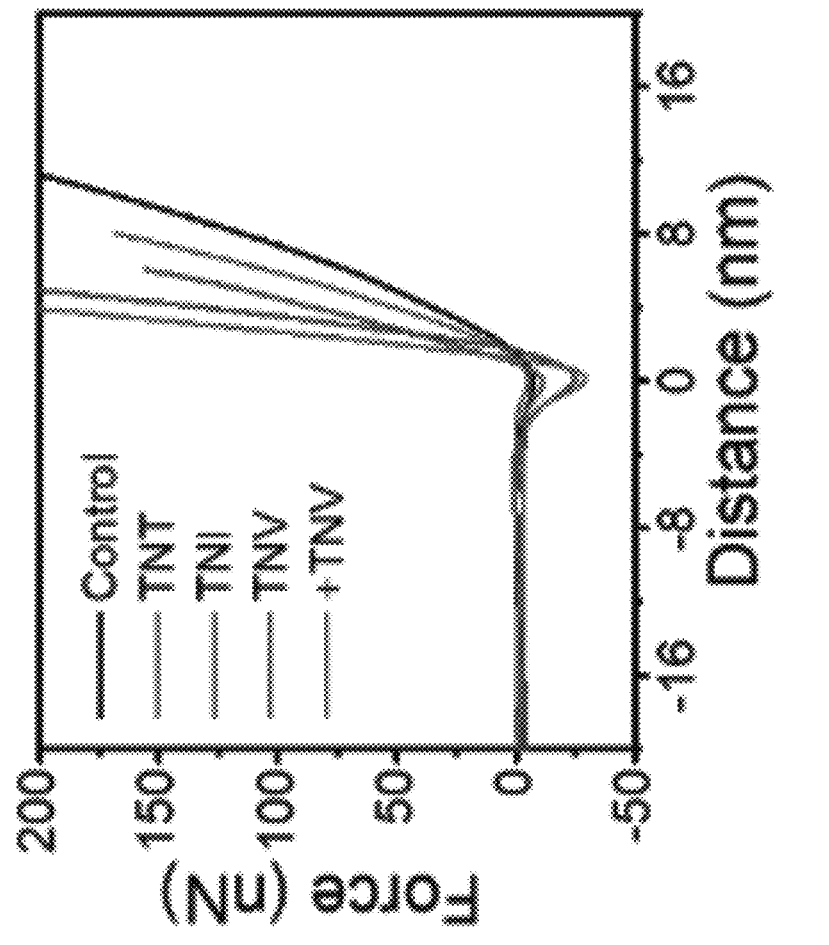
Figure 4D:
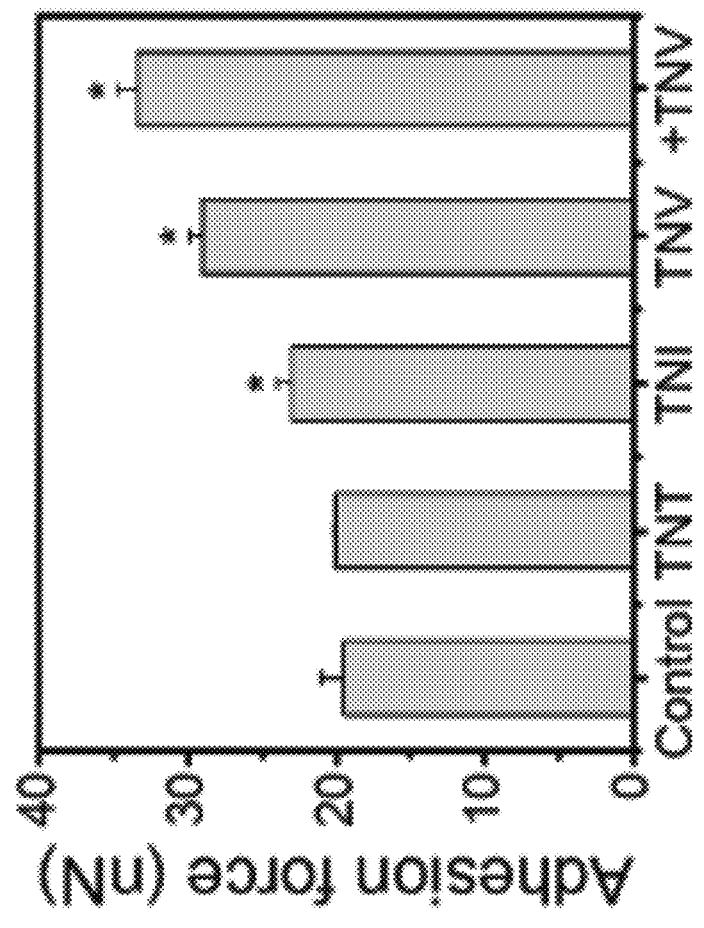
Figure 4E:
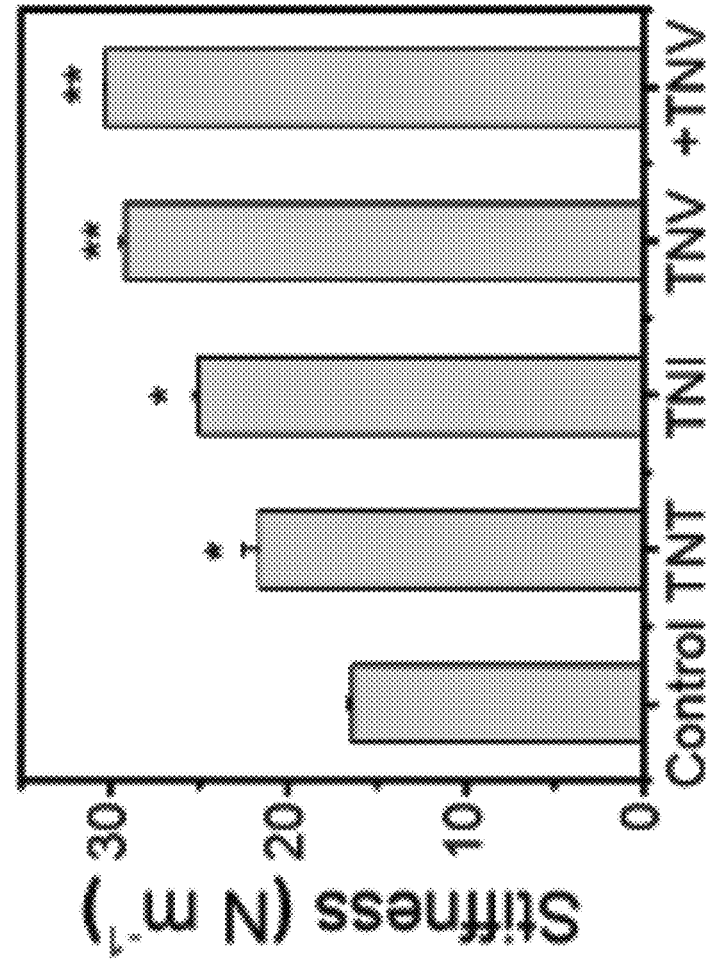

The antibacterial trend from TNT to +TNV is investigated quantitatively by AFM. The force-distance curves show both the adherence force and bacterial stiffness. The nonlinear portion in the retraction curve is used to determine the adhesion force between the bacteria and substrate (FIG. 4B) and the retracted curve in FIG. 4C conveys semi-quantitative information. The adherence force between the titanium plate and bacteria is the weakest, but increases on the nanowires or charged surface. The quantitative results in FIG. 4D show that the adherence force on the control and TNT is about the same of 20 nN and that on TNI increases to 23 nN. It continues to increase by more than 50% to 30 nN and 35 nN on TNV and +TNV, respectively. Besides, the stiffness of the bacteria membrane is elevated in the order of control<TNT<TNI<TNV<+TNV with significant differences in all the experimental groups compared with the control group (FIG. 4E). The stiffness is closely related to the extension force imposed on the outer membrane. For a small tension, self-adjustment of the flexible membrane maintains the area but when the tension increases so high that membrane undulation is no longer possible, the stiffness increases exponentially. Owing to the strong tension on TNV and even stronger tension on +TNV, the stiffened membrane becomes crisp and fragile.

3. Simulation of the Interactions and Influence on Membranes

Figure 4F:
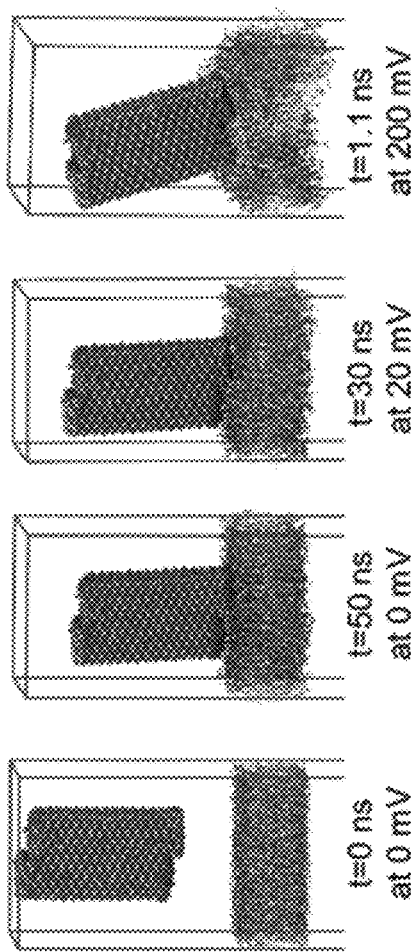

The bacteria-surface interactions are analyzed by molecular dynamic simulation. Without applying an electric field to the bilayer in the nanowire system (FIG. 4F), it takes 50 ns for the nanowire to get in close contact with the membrane bilayer. The introduction of an electric field significantly increases the approach velocity. At 20 mV, the nanowire interacts with the bilayer for 30 ns but still does not translate through it (FIG. 4F). However, when the electric field is increased to 200 mV, the same nanowire takes only 1.1 ns to translate and break the bilayer (FIG. 4F). A small morphological change is observed from the bilayer at 20 mV, while the bilayer suffers serious distortion at 200 mV.

Figure 4G:
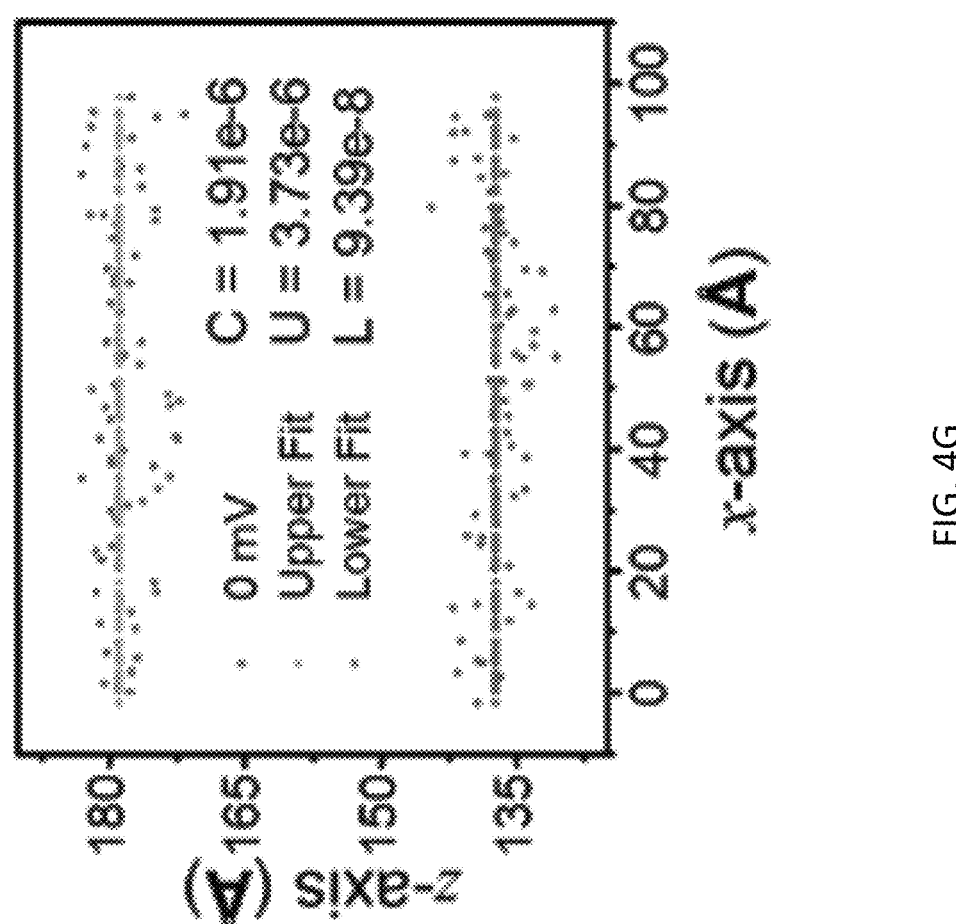
Figure 4H:
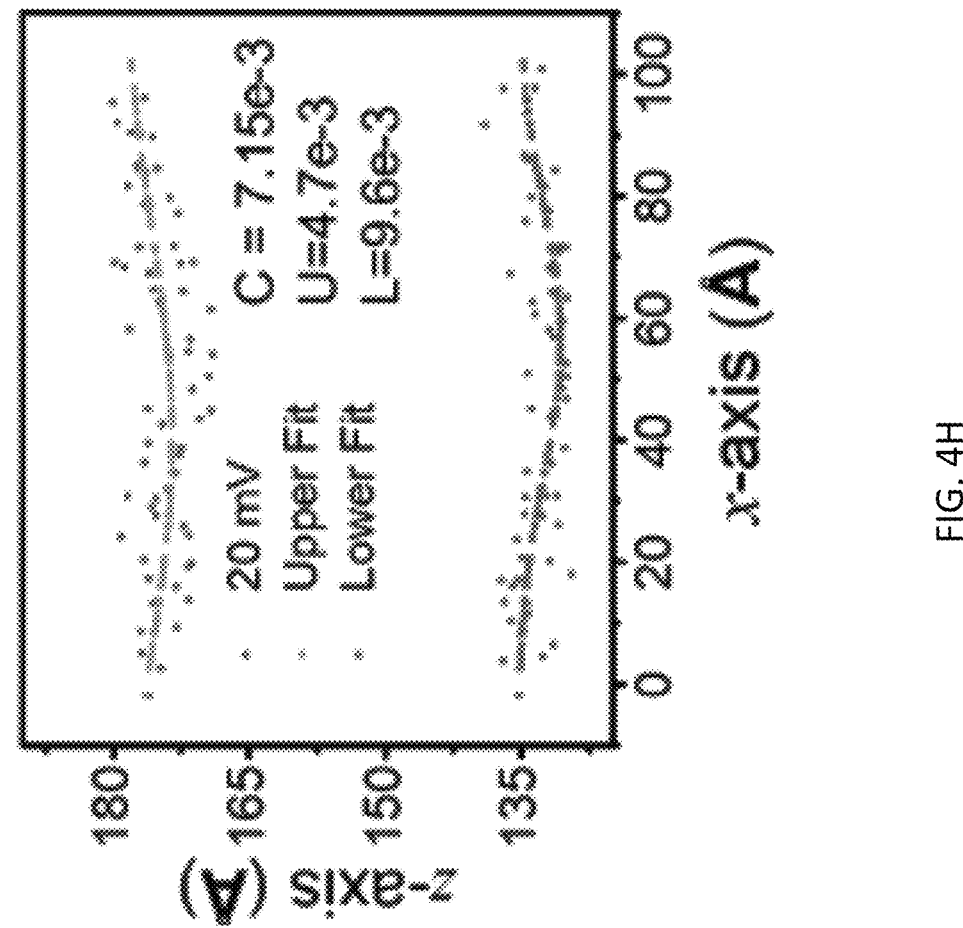
Figure 41:
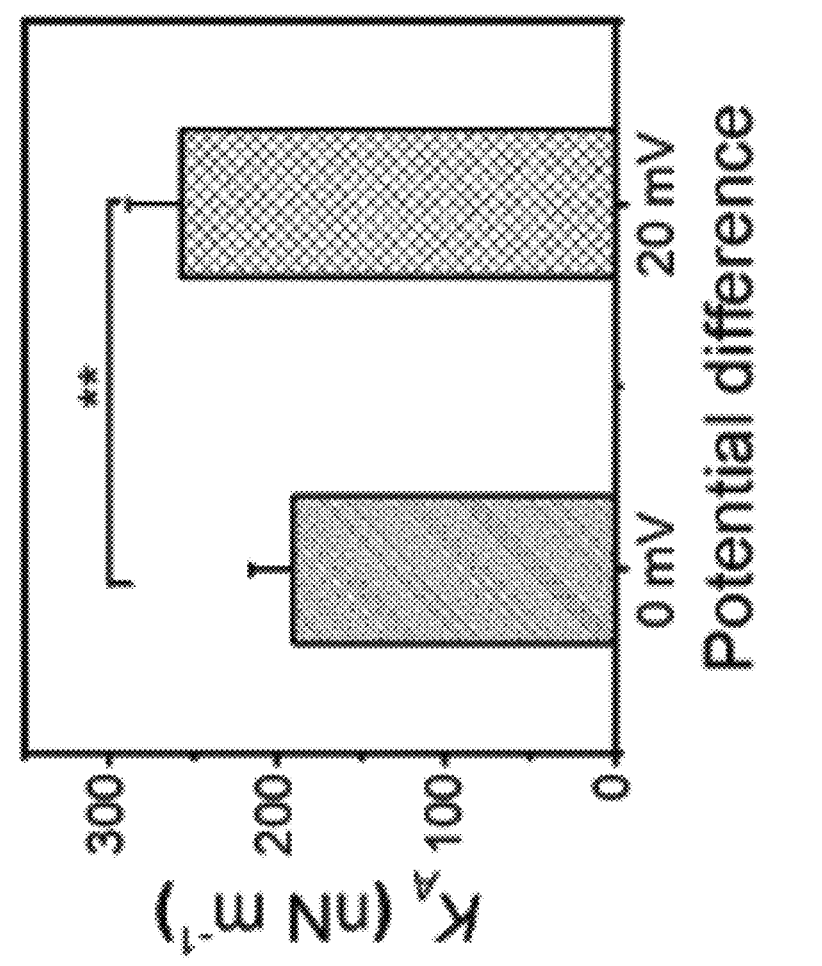

Membrane distortion is quantitatively analyzed on the nanosecond scale by calculating the Gaussian curvature in the system (FIGS. 4G and 4H). The Gaussian curvature increases from $1.91 \times 10^{-6}$ (Upper=$3.73 \times 10^{-6}$, Lower=$9.39 \times 10^{-8}$) for the bilayer membrane in non-voltage simulation to $7.15 \times 10^{-3}$ (Upper=$4.7 \times 10^{-3}$, Lower=$9.6 \times 10^{-3}$) for 20 mV, confirming the narrowed and rugged interface as a result of electrostatic interactions. The area compressibility $K_A$ of the treated bilayer which is correlated positively with the stiffness is considered (FIG. 4I). $K_A$ increases from 190±25.1 mN m$^{-1}$ for the non-voltage trajectory to 256±32.1 mN m$^{-1}$ for 20 mV. Both the enhanced curvature and $K_A$ contribute to a stiffer membrane making it easier to be penetrated and destroyed. All in all, the simulation results are consistent with the experimental data, illustrating that +TNV has stronger adhesion force to narrow the interface and the stiffer membrane renders it more susceptible to disruption.

The adhesion strength at the interface is important for bacteria destruction and a larger adhesion force may lead to a higher probability of rupturing for the same nanostructure morphology. When bacteria are in contact with the nanowires, they will try to settle on the rugged and stiff surface by increasing the contact area and anchor on multiple points (red arrows in FIG. 3F). However, this stretching process may exert surface tension surpassing the threshold of the bacteria membrane, in which case cell rupture can take place at any time. The electrical attraction between the charged TNV and bacteria makes the rugged surface tougher and as a result, serious membrane collapse arising from the maximum electro-mechanical stress is observed from +TNV. Hence, the electro-mechanical interactions on +TNV accentuate the mechanical disruption of the bacteria.

Biochemical Antibacterial Mechanism

Apart from the mechanical force exerted on bacteria, the electrically charged surface may interact with the negatively charged outer membrane of bacteria causing electron disbalance. To explore the potential difference at the interface and ensuing physical changes of the bacteria, the membrane potential and intracellular electron density are determined.

1. Membrane Potential Reduction

Figure 5A:
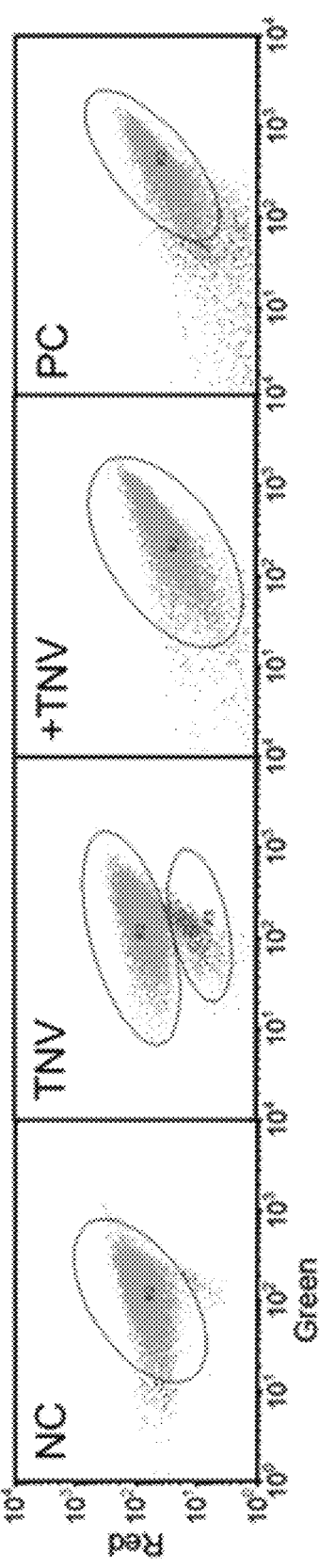
Figure 5B:
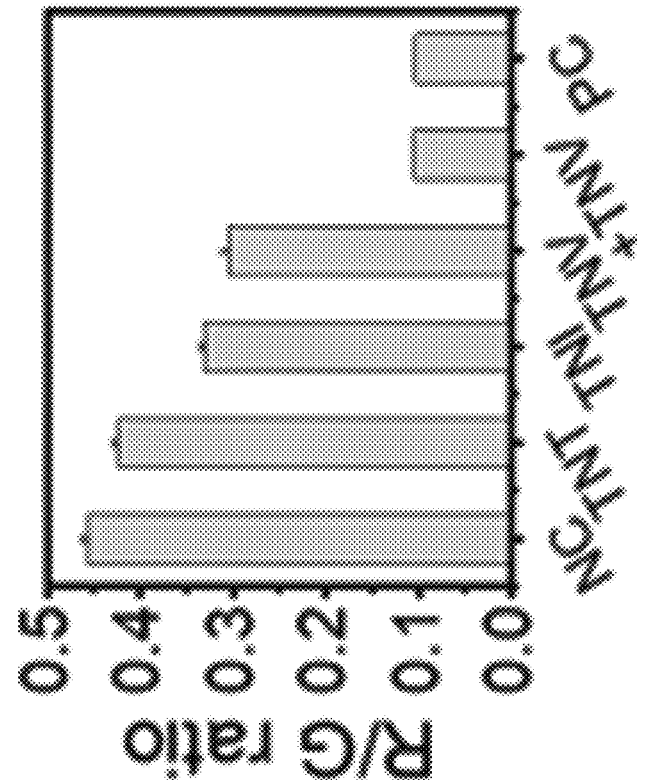

The membrane potential which is an indicator of the polarization state of bacteria can be expressed by the Red/green (R/G) ratio after staining by DiOC$_2$(3). As potassium is the dominant factor in the membrane potential and the concentration of potassium is larger inside the bacteria than outside, normally polarized bacteria are supported by a negative membrane potential with a relatively large R/G ratio. As shown in FIG. 5A and FIG. 15, the membrane potential on the control and TNT is about the same, but on TNI and TNV, the bacteria are distributed in two regions (R2 and R3). The membrane potential of R2 is similar to that of the control group, but that of R3 decreases significantly, revealing that TNI and TNV disrupt the bacteria upon direct contact. However, other bacteria that do not make direct contact are not affected. When TNV is charged before bacteria culturing, the whole quorum of bacteria is marked with a significantly reduced R/G ratio similar to the positive control group (PC), indicating that +TNV influences bacteria in the wider range than TNV. The corresponding quantitative results are presented in FIG. 5B. The slightly reduced R/G ratio can be explained by the mechanical damage to the adhered bacteria at the very top of TNI and TNV, whereas more than 3 times reduction of R/G is observed from +TNV on account of the enhanced mechanical and electrical interferences on the bacteria. The membrane potential difference among the groups suggests that the nanomechanical interactions at the interface slightly neutralizes the resting potential by increasing the membrane permeability, while addition of positive charges decreases the permeability and triggers instantaneous electron transfer through the membrane, giving rise to multiplied reduction of the R/G ratio, which is consistent with the results reported previously.

2. Intracellular Electron Distribution

The biochemical change rendered by the electro-chemical interaction is further examined by performing TEM on the sliced bacteria (FIG. 5C and FIG. 16). Bacteria suffer from increasing membrane disruption in the order of TNT, TNI, TNV and +TNV (black arrows in FIG. 5C). Besides, electrons are distributed uniformly on the other samples, while +TNV shows obvious electron-light regions corresponding to electrical disbalance in the membrane potential test (area circled in red in FIG. 5C). The results verify that while TNI or TNV causes only limited mechanical damage to the bacteria, addition of electrical charges accentuates the mechanical interaction and also triggers electron flow in a specific direction. As a result, +TNV poses the harshest microenvironment for bacteria. The membrane potential is fundamental to the proton motive force in bacteria to regulate cell division and therefore determines the living state of bacteria. With regard to +TNV, the electric field between the positive charges on the materials surface and negative outer membrane stimulates electron flow from the bacteria to the outside as indicated by the electron light regions.

3. Intracellular Oxidative Stress by Electron Interference

Figure 5D:
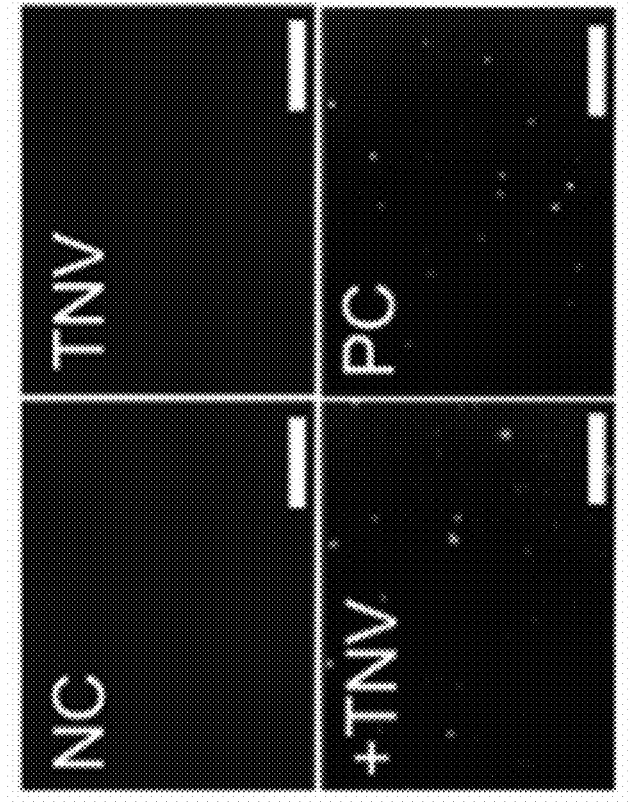
Figure 5E:
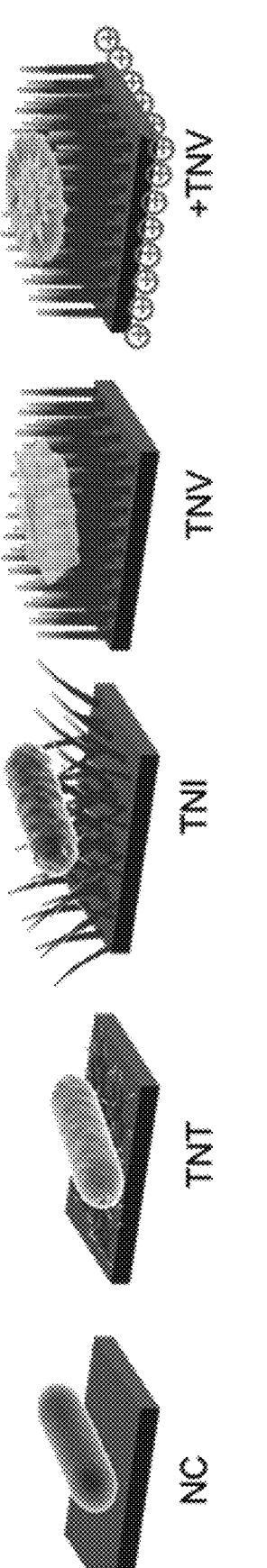

Dissipation of the membrane potential influences the availability to utilize oxygen as the electron acceptor and disorganizes the intracellular oxidative level (FIG. 5D and FIG. 17). While TNT, TNI and TNV are similar to the negative control showing no intracellular ROS spot, +TNV exhibits similar results as the positive group showing significant green spots. ROS staining indicates that the nanowires with different orientations only disturb the integrity of the membrane, whereas electron transfer is an important factor influencing the oxidation level. As electron suppliers, the components inside the bacteria are oxidized when electrons are depleted by the positively charged surface. The internal ROS level is raised by a series of biochemical reactions which consume a lot of energy and starve the bacteria to death as a second attack besides mechanical damage. The schematic diagram showing how the bacteria are affected by different surfaces is depicted in FIG. 5E.

4. In Vitro Cytocompatibility

+TNV fares the best in the antibacterial assessment and preliminary in vitro cell experiments and there is indication that none of the TN samples adversely affect adherence and proliferation of osteoblasts and even foster growth of osteoblasts as indicated by MTT (FIG. 18A). The cytoskeleton of the osteoblasts after culturing for 24 h is observed after fluorescent staining (FIG. 18B). The osteoblasts on the four TN samples adhere and proliferate well with the spreading filopodia showing a larger area than the control. The magnified SEM image shows consistent results (FIG. 18C). Comparing the electrically charged and uncharged group, no significant difference can be found illustrating that it is the nanostructure that enhances adhesion and proliferation of osteoblasts.

In Vivo Evaluation of Antiinfection and Antiinflammation

Figure 6A:
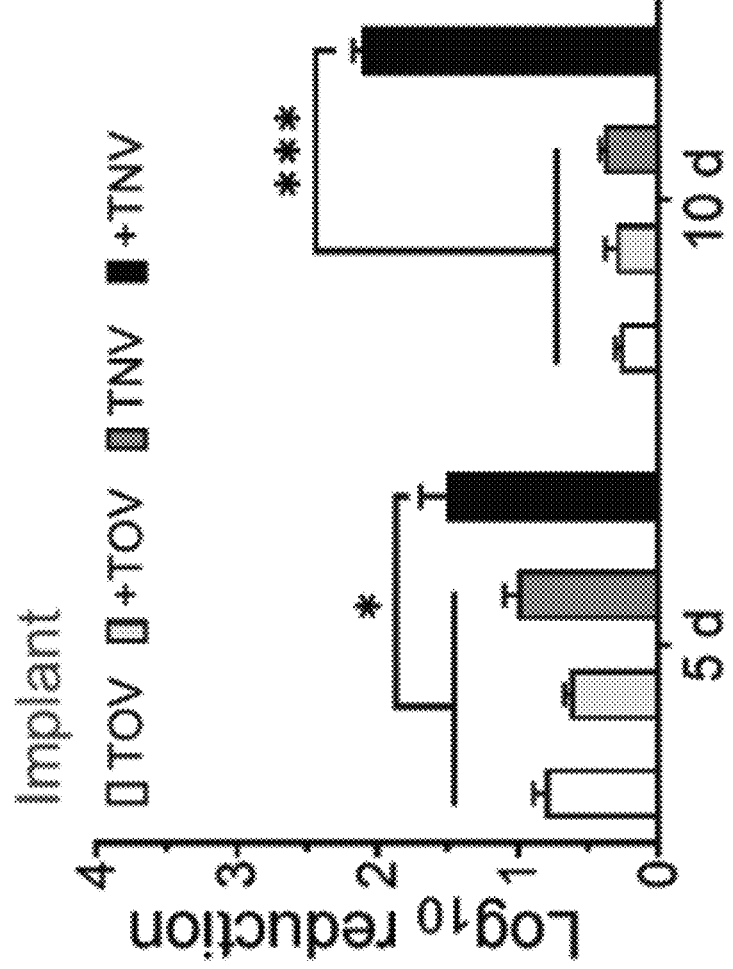
FIGS. 6A-6C show in vivo experiments evaluating anti-infection and anti-inflammation. Antibacterial results from FIG. 6A Surgical implant and FIG. 6B surrounding tissues 5 and 10 days after bacteria challenge.
Figure 6B:
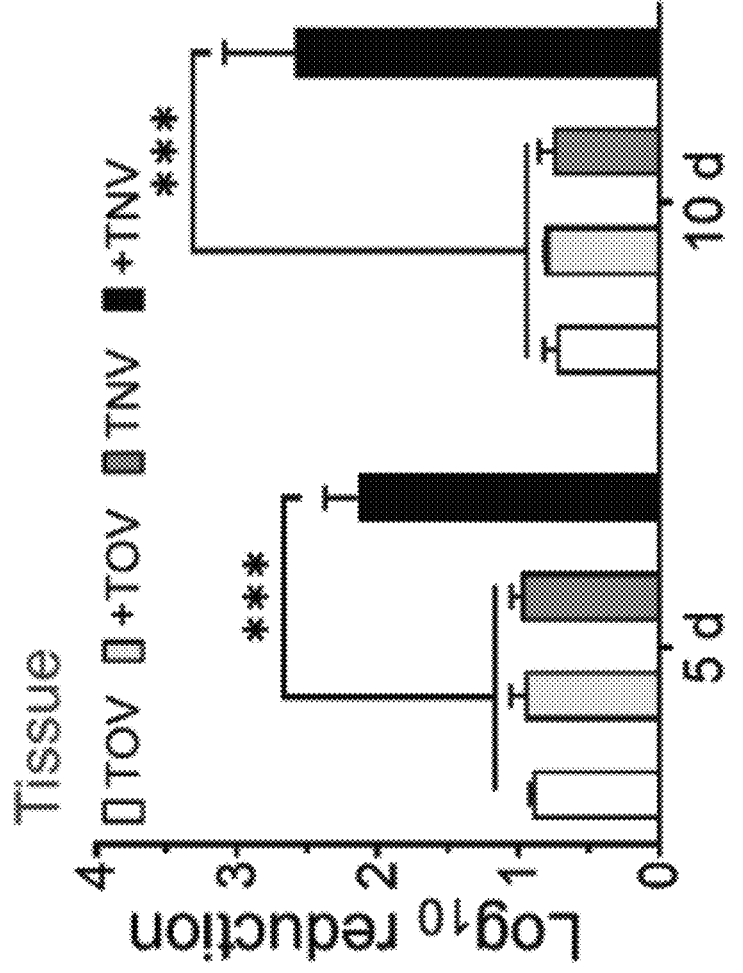
Figure 6C:
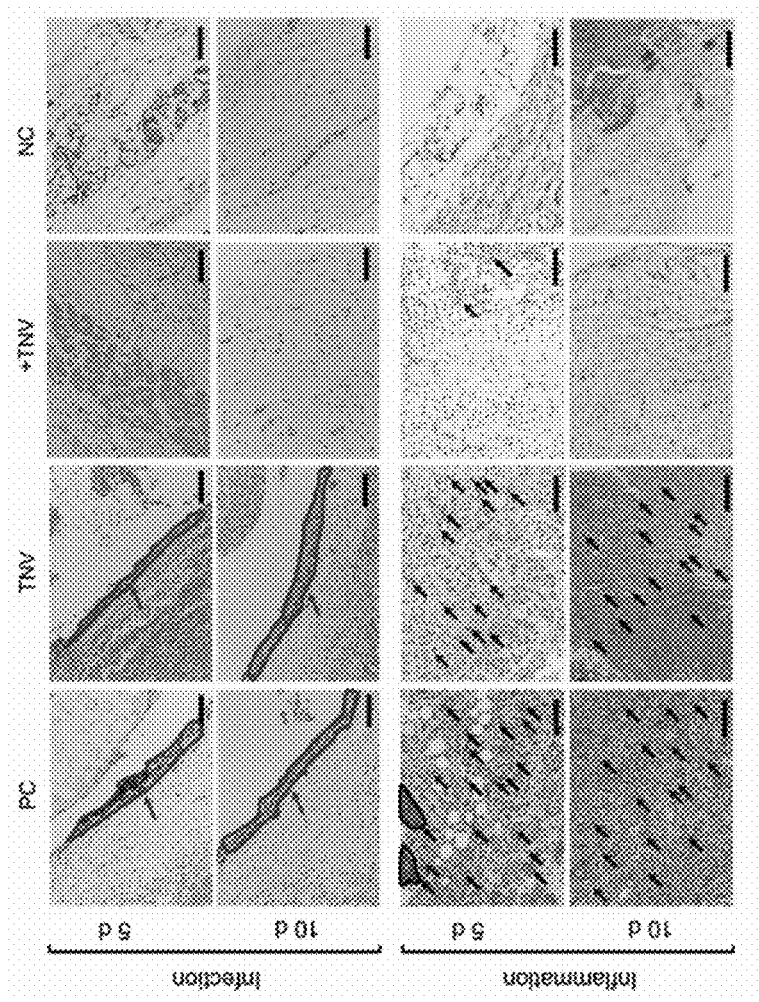
Figure 7A:
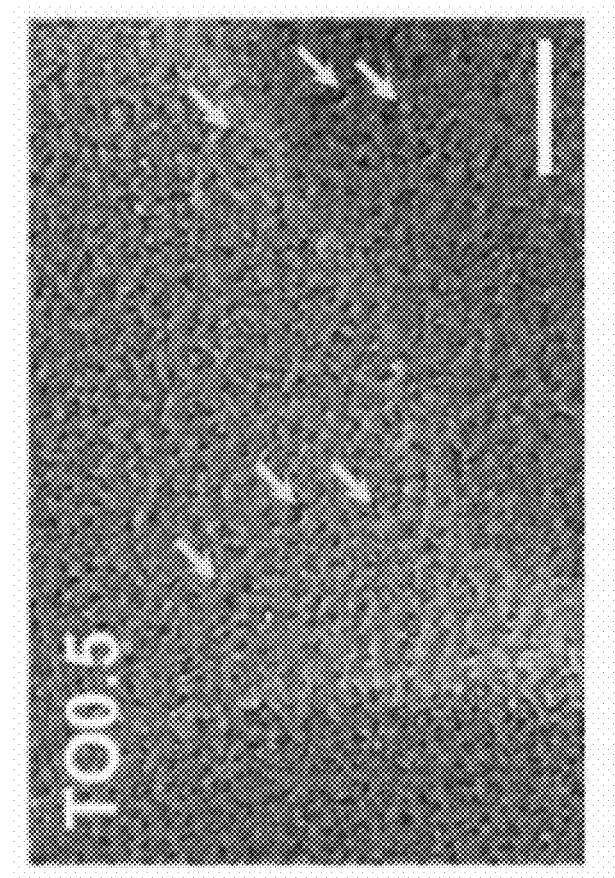
FIGS. 7A-7D show the changes in the surface morphology during the first 2 hours. Some of the nanopores and nanowires are indicated by yellow and white arrows and show that the process starts with erosion and dissolution in the first hour. Afterwards, nucleation occurs and gradually becomes dominant. After 2 hours, nanowires are formed on the surface (scale bar=500 nm).
Figure 7B:
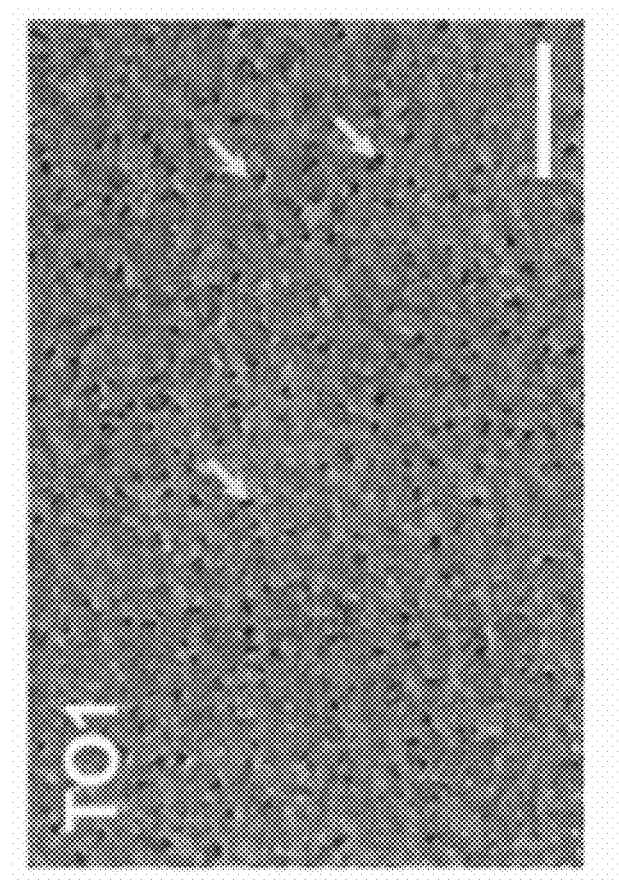
Figure 7C:
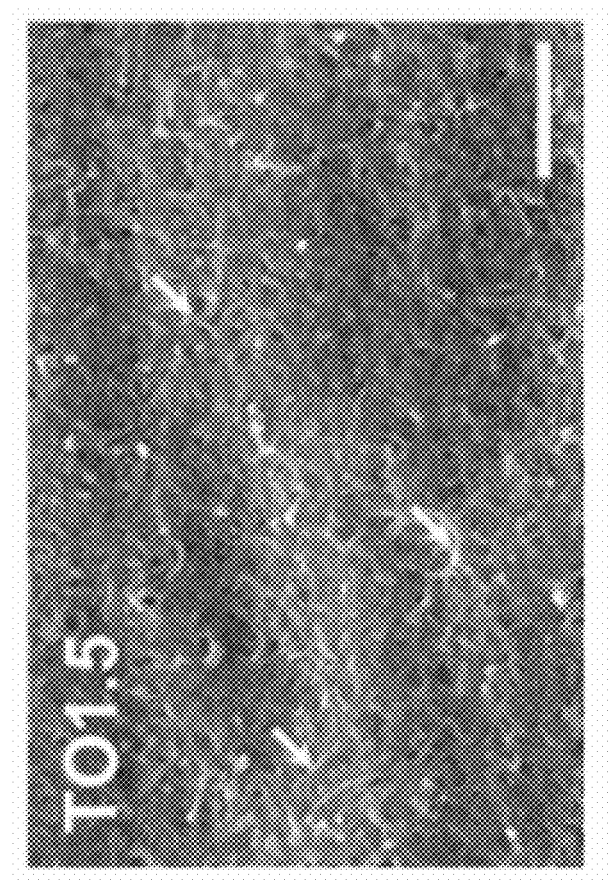
Figure 7D:
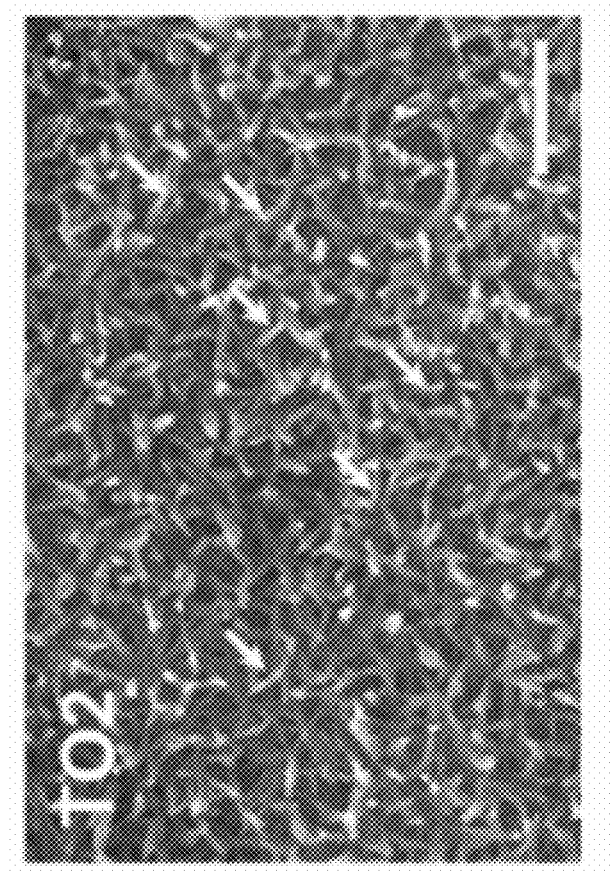

An infection animal model is implemented with implant- and tissue-related bacteria for 5 and 10 days counted. Although more than 75% of the bacteria on the implants and tissues in all the samples can be inactivated during the first 5 days (log reduction >0.6), bacteria that escape initial death proliferate subsequently on TOV, +TOV, and TNV. However, the antibacterial rate of +TNV is maintained to be 99% (log reduction >2), illustrating that the combination of nanomechanical force and electron transfer synergistically inhibits bacteria proliferation (FIGS. 6A and 6B). The excellent antibacterial efficiency of +TNV leads to healthy recovery without significant fibrous layers or inflammation. In contrast, a large number of bacteria survive on TNV. The fibrous layer is as thick as that in the positive control (FIG. 6C, area circled in red). Consequently, infection triggers the immunological system resulting in aggregation of lymphocytes (black arrows in FIG. 6C). The in vivo results corroborate the in vitro analysis and the synergistic effects rendered by the mechanical and electrical interactions are preserved in vivo.

The outer membrane determining the stiffness and strength of bacteria has been thoroughly investigated from biophysical and biochemical perspectives to determine the physical interaction of the nanowire system is taken full advantage of by combining mechanical and electrical disruption. TNV with considerable capacitance is verified electrochemically and the electrostatic force is demonstrated to be sufficient to cause membrane damage in concert with mechanical stress. The rugged topography formed by the nanowires exerts enhanced stretching forces on the membrane and the elevated stiffness increases the damage to the bacteria (FIGS. 3 and 4). The experimental data are supported by theoretical simulation that when the potential difference is increased from 0 to 200 mV, more close contact is created in 1.1 ns and a remarkable transformed bilayer with increased Gaussian curvature and $K_A$ indicates stiffened membrane. The sufficient mechanical contact reinforces electron transfer as validated by the membrane potential and light regions inside the bacteria observed from +TNV (FIG. 5). The electrical disbalance contributes to oxidation-reduction turbulence in the intracellular part exhibited as elevated ROS on +TNV but not the other groups. Hence, the bacteria in the comparatively large vicinity experience membrane and intracellular disruption causing death. The experimental and theoretical investigations provide quantitative information on how nanomechanical and electrical stress can be tuned in concert to boost the antibacterial ability and mitigate bacterial infection.

In summary, capacitive nanowires with different orientations are produced controllably to enhance the antibacterial properties by exploiting the physical and electrical effects at the implant-bacteria interface. Compared to the tiled and inclined nanowires (TNT and TNI) showing log reduction of less than 0.4, nanowires with the vertical orientation (TNV) kill 0.6 log of the bacteria by stretching the bacteria membrane. The antibacterial efficiency can be further enhanced by 5 times to 3 log reduction by charging the capacitive TNV (+TNV) and the latter process is demonstrated to prevent bacterial infection in vivo in rats. The systematic biophysical, electrochemical, and biochemical analyses indicate that the electrical interactions not only supplement mechanical damage by accentuating the electrostatic attraction between the bacteria and implant surface, but also facilitate electron flow from the bacteria to the materials to enhance intracellular ROS production. As result, bacteria die from the double effects of membrane damage and intracellular oxidative stress. The biophysical and biochemical analysis enriches our fundamental knowledge about the electro-mechanical stress on bacteria and provides insights into the development of non-leaching antibacterial implant materials with clinical significance.

EXAMPLES

Preparation of Titanium Oxide/Nitride Nanowires

The titanium dioxide nanowires were synthesized by a wet oxidation process. A solution of melamine (0.004 g mL-1), hydrogen peroxide (30 wt %), and nitric acid (65 wt %) with a volume ratio of 25:25:1 was mixed ultrasonically.

Afterwards, clean titanium plates were placed horizontally or vertically into the solution (ratio of titanium plates to the solution is 1 cm² to 1 mL of the solution). The synthesis was carried out in a blast oven at 80° C. for 0-10 h and tiled, inclined, and vertical titanium oxide (TO) nanowires were formed on the substrate by adjusting the initial orientation and reaction time. The samples were labeled TOT, TOI, and TOV, respectively. After the reaction, the samples were washed with deionized water and dried at room temperature. TO was then annealed in a tube furnace at 850° C. for 1.5 h in air atmosphere for stabilization. The unannealed TO was treated under nitrogen in a tubular furnace. The sample was placed on a corundum crucible in the tubular furnace and the corundum crucible contained 5 g of urea and placed at a distance of 3 cm in the upwind direction. The nitrogen treatment was carried out at 850° C. for 1.5 h under flowing nitrogen (50 sccm) at a heating rate of 5° C. min-1. The titanium nitride (TN) samples were obtained after cooling in the furnace and designated as TNT, TNI, and TNV, respectively.

Morphological Characterization

The morphology of the samples was examined by scanning electron microscopy (SEM) (XL30, ESEM-FEG, Philips, Holland) and atomic force microscopy (AFM) (Veeco MultimodeV). The chemical states were determined by X-ray photoelectron spectroscopy (XPS) (K-Alpha, Thermo Fisher Scientific, USA) with Al $K_\alpha$ radiation referenced to the Ar 2p peak at 242.4 eV. Elemental depth profiling was performed by XPS using an approximate sputtering rate of 31.5 nm min-1. The composition and crystallinity of the samples were determined by X-ray diffraction (XRD) (SRD-D2 Phaser, Bruker, Germany) with Cu $K_\alpha$ irradiation ($\lambda$=1.54184 Å) at 30 kV and 10 mA and Raman scattering (Horiba Jobin-Yvon Lab Ram HR VIS high-resolution confocal Raman microscope with a 633 nm laser as the excitation source). High-resolution images were acquired at 200 kV by field-emission STEM (JEOL JEM-2010F) to reveal the lattices.

Electrochemical Characterization

The electrochemical properties of the samples were determined using a three-electrode system on an electrochemical workstation (CHI660, Chenhua, China) in LB to mimic the bacterial growth environment. The sample (1 cm×1 cm), platinum wire, and saturated calomel electrode (SCE) served as the working electrode, counter electrode, and reference electrode, respectively. Cyclic voltammetry (CV) was carried out from −1 to 1 V at a scanning rate of 100 mV s⁻¹ and galvanostatic charge-discharge (GCD) tests were performed at a constant charging current of 0.1 mA cm⁻². A one-time discharging curve of the charged (charged to 1 V) sample was recorded for 4 h with the working electrode and counter electrode separated by 1 cm. The discharging capacities of the charged samples were calculated by the line integral.

Antibacterial Analysis

The antibacterial activity of the sterilized samples was assessed with Gram-positive (Staphylococcus aureus, 29213) and Gram-negative (Escherichia coli, ATCC 25922) bacteria. The pure bacteria in LB were cultivated overnight in a rotating shaker at 37° C. and cultivated to a concentration of 1× 109 CFU mL⁻¹ ($OD_{600}$=0.2 for S. aureus and $OD_{600}$=0.2 for E. coli). The bacteria solution was diluted for the antibacterial test. The samples were immersed in 75% alcohol for 30 min for sterilization and dried in nitrogen before they were prepared on the anode of the reaction kettle. After 6 h, the adhered bacteria were detached from the surface with 900 μL of the saline solution, diluted to the proper concentration, spread on a solid agar plate, and cultivated for another 18 h to count the CFU. To determine the antibacterial efficiency after electrochemical interactions, the samples were charged for 20 min immediately before the bacteria cultivation. The antibacterial rate was determined by the following formulas: Antibacterial rate= (1−$CFU_{experimental\ group}$/$CFU_{control\ group}$)×100%; $Log_{10}$ reduction=−$log_{10}$ (1−antibacterial rate).

After bacterial cultivation for different durations, the samples were treated with 2.5% glutaraldehyde overnight and dehydrated with a series of gradient alcohol solutions (30, 50, 75, 90, 95, and 100%) for 10 min sequentially before drying at room temperature. The integrity and morphological changes of the bacteria were observed by SEM.

Live/Dead and Intracellular ROS Staining

The bacteria on the samples were stained by the LIVE/DEAD® BacLight™ Bacterial Viability Kit (L-7012, Molecular Probes, Thermo Fisher Scientific, USA) after cultivation. The live bacteria were stained green and dead bacteria were stained red. 15 min after staining, the samples with bacteria were gently washed with PBS to remove the excess dye and put on a glass slide for observation under an inverted fluorescent microscope (BM-20AYC, BM) with 488/520 nm and 488/630 nm as the excitation/emission wavelengths for green and red fluorescence, respectively.

In the intracellular ROS staining experiment, the bacteria on the samples were washed with PBS three times and stained with 2', 7'-dichlorodihydrofluorescein diacetate (DCFDA, Beyotime, China) for 15 min in darkness. The excess dye was removed by PBS and the samples were observed under an inverted fluorescent microscope with 488 nm as the excitation wavelength and 520 nm as the emission wavelength.

Inner Structure of the Bacteria Examined by TEM

After incubation, the specimens were treated ultrasonically for 5 min in PBS to dislodge bacteria from the sample surface. The solution was centrifuged for 5 min (4,000×g) to collect the bacteria from the bottom. The bacteria were fixed successively with 2.5% glutaraldehyde and 1% $OsO_4$ at room temperature overnight. After washing with PBS and dehydration with alcohol and acetone with gradient concentrations, the samples were embedded in Spurr's resin (Spurr Embedding Kit, Spurr, USA) before slicing into sections (<100 nm thick) with a glass knife and staining with uranylacetate. The stained samples were placed on a copper wire mesh and examined by TEM (TecnaiG²12 BioTWIN, FEI company, USA) at 120 kV.

Membrane Potential Test

The potential of the bacteria membrane was evaluated by a membrane potential kit (B34950, Invitrogen, USA) with the bacteria treated with CCCP serving as the positive control. The bacteria depolarization level was qualitatively characterized as the dots in flow cytometer and quantitatively calculated as the red/green fluorescence ratio.

Nanomechanical Analysis by AFM

After the antibacterial procedures, the samples with bacteria were analyzed by AFM (Veeco, CA, USA). The cantilevers were pyramidal probes with a spring constant of 0.05 N m⁻¹ and the front and back angle was 35° (Veeco Instruments Ltd., Cambridge, UK). AFM was conducted in the tapping mode with the cantilever erased across the surface. The measurements were taken at 1 Hz from an area of 5 μm×5 μm. 3D topographical images were reconstructed according to the survey maps. Afterwards, the AFM tip was located on the bacteria and the AFM force measurements were performed to obtain the force-distance curves, where the distance traveled by the tip was plotted against the deflection of the cantilever. The adhesion force and stiffness of the membrane were derived by analyzing the non-linear and linear parts of the retraction curves.

Molecular Dynamic Simulation

In the simulation, rutile 101 surface titania nanoparticles were selected from which were cut to a 50 Å×20 Å×90 Å nanowire shape for simplicity and with a charge of +129 on the top and bottom surfaces. The force field parameters for the titania rutile 101 surface were also modified accordingly.

In order to mimic the bilayer performance for the bacteria, the membrane components of 1-palmitoyl-2-oleoyl-sn-glycero-3-phosphoethanolamine (POPE, neutral lipid) and 1-palmitoyl-2-oleoyl-sn-glycero-3-phospho-(1'-rac-glycerol) (POPG, −1 charged lipid) with a ratio of 3:1 were selected for each leaflet. The main component of the bacteria was POPE with about 25% charged lipids chosen as POPG. The POPE and POPG lipids were modeled using the CHARMM36 lipids force fields and CHARMM TIP3P water model. The bilayer and nanowire were solvated in 150 mM KCl solution and the simulation was performed with the GROMACS 2016.4 engine using a 1 fs time step. The overall workflow of the simulation included initial construction of the energy minimization, isothermal-isochoric (NVT) and isothermal-isobaric (NPT) equilibration runs, and NPT production runs. NVT simulation was carried out for 25 ns at 310.15 K and NPT equilibration simulation proceeded for 5 ns, followed by 50 ns NPT production run without a voltage. The electrostatic interactions were calculated by Particle Mesh Ewald (PME) summation. A cutoff of 1.2 nm was used to calculate both the short-range electrostatic and van der Waals interaction with the Potential-shift-Verlet algorithm applied to smoothly shifting beyond the cutoff. The long-range electrostatic interaction was calculated by the reaction-field algorithm implemented in GROMACS. The neighbor list was updated every 20 steps using a neighbor list cutoff equal to 1.0 nm for van der Waals. The temperature of each group (protein, membrane, titania, ions, and water) was kept constant by the Nose-hoover algorithm with a 5 ps time constant. The pressure was maintained at 1 bar using a semi-isotropic Berendsen barostat with a relaxation time constant of 10 ps and the three-dimensional periodical boundary conditions (PBC) were adopted. To identify the interactions between the bilayer membrane and titania nanowires under a voltage, voltage simulation of 20 mV and 200 mV was conducted after 50 ns non-voltage run. The voltage in GROMACS 2016.4 was set through E-z and for the 20 mV and 200 mV voltages, the simulation was carried out for 30 ns and 5 ns, respectively.

The area compressibility $K_A$ is an important mechanical property of a bilayer that quantifies the response of membrane area to tension. In the symmetric bilayer with minimum undulations (the difference in projected areas and local areas is negligible), the area compressibility $K_A$ can be evaluated from the mean square fluctuation of the total area of the bilayer or the probability distribution of the area change around the mean. Here, $K_A$ was calculated based on local thermal fluctuations of the leaflet thickness. In this approach, each leaflet was viewed as a collection of more than one parallel elastic block with the same average area but different instantaneous areas. The interleaflet coupling was shown to be equivalent to the variance of the bilayer area A ($\sigma^2(A)$) and the local area fluctuation was then converted to the local thickness fluctuation assuming volume conservation. The curvature was also closely related to the mechanical property of the bilayer and the Gaussian curvature after simulation was calculated according to a previous study.

In Vitro Biocompatibility Evaluation

The MC3T3-E1 osteoblasts obtained from the cell bank of the Chinese Academy of Sciences were used to study the biocompatibility of the samples in vitro. The cells were nurtured in the culture medium containing the Dulbecco's modified eagle medium (DMEM) and 10% fetal bovine serum (FBS) and incubated in a humidified atmosphere of 5% $CO_2$ at 37° C. with the medium refreshed every other day. The cells in the logarithmic growth phase were harvested, centrifuged for 5 min, and diluted to $2\times10^4$ cells mL-1. The samples were disinfected and 1 mL of the cell solution was seeded on a 24-well plate. The MTT assay was employed to evaluate the cell viability. After cultivation for 1 day, 4 days, and 7 days, the medium on the 24-well plate was removed and 1 mL of the MTT solution was added to each well. After further incubation for 4 h, the MTT solution was replaced with the DMSO solution to dissolve the formazan crystals. Subsequently, 100 μL of the solution was transferred to a 96-well plate and the optical density at 570 nm was measured on a multimode reader (EON, BioTek, USA) with DMSO as the negative control. To assess adhesion, the cells were rinsed with PBS twice, fixed with 4% paraformaldehyde, permeabilized with 0.2% Triton X-100 (Sigma, USA), stained with phalloidin-fluorescein isothiocyanate (Sigma, USA) for 60 min, and then stained with 4',6-diamidino-2-phenylindole (DAPI, Sigma, USA) for 5 min. The samples were observed under an inverted microscope (20AYC-BM, BM). The samples with cells were also fixed and examined by SEM to evaluate the morphology of the osteoblasts.

In Vivo Assessment of the Antibacterial Efficacy, Anti-Inflammatory Effects, and Biocompatibility Male 12-week-old SD rats (200-300 g) maintained in the animal room under specific pathogen-free (SPF) conditions were used in the in vivo assessment. Before surgery, the animals were housed for 1 week for acclimatization. All the animal experiments were carried out under sterile conditions and approved by the Ethics Committee for Animal Research, Shenzhen Institutes of Advanced Technology, Chinese Academy of Sciences. They were anesthetized with pentobarbital sodium (45 mg kg-1) via intraperitoneal injection before the hair was shaved from a 3 cm×5 cm area and sterilized with povidone iodine. After incising the skin layer-by-layer parallel to the spine, the samples (10 mm×10 mm×1 mm) were implanted into the subcutaneous soft tissue. The skin incisions were sutured before *S. aureus* 100 μL of PBS ($10^7$ CFU mL-1) were injected around the implant. The inflammatory response was examined daily and after 5 and 10 days, the rats were euthanized. The implants were collected, immersed in PBS, and shaken for 2 min on a vortex shaker to count the implant-related CFU. Meanwhile, the surrounding soft tissues were immersed in PBS and homogenized (Scientz-IID, Ningbo, Zhejiang, China) for CFU counting. In the histological observation, other parts of the soft tissues were fixed with 10% buffered formalin, washed with PBS, dehydrated in gradient alcohol, embedded in the paraffin, and sectioned. The sections were deparaffinized and stained with H&E and Gram stain before observation by optical microscopy. The infection and inflammation states were evaluated by comparing the distributions of bacteria and lymphocytes, respectively.

Statistical Analysis

The data were presented as mean±standard deviation (SD, n=3). The data were evaluated by the t-test and Tukey test in ANOVA with the software of OriginPro 2016. Differences of P<0.05 and P<0.01 were considered significant and highly significant, respectively.

It should be apparent to those skilled in the art that many modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "include", "including", "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. An antibacterial implantable medical device or medical material, comprising:

a surface;

a titanium coating; and titanium nitride nanowires extending from the titanium coating at a selected angle, wherein the titanium nitride nanowires are initially grown on the titanium coating as titanium dioxide nanowires and subsequently converted to the titanium nitride nanowires after being exposed to a nitrogen-containing atmosphere at an elevated temperature, wherein the titanium nitride nanowires are grown such that they extend at a selected angle of between 60 degrees and 90 degrees from the titanium coating, and wherein the titanium nitride nanowires are configured to exert a combination of mechanical force and localized electrical interference on bacteria bilayer membranes sufficient to at least partially disrupt the bacteria bilayer membranes.

2. The antibacterial implantable medical device or medical material of claim 1, wherein the selected angle is an 90 degree angle.

3. The antibacterial implantable medical device or medical material of claim 1, wherein the titanium coating and/or the titanium nitride nanowires are charged.

4. The antibacterial implantable medical device or medical material of claim 1, wherein the implantable medical device is a bone fastener.

5. The antibacterial implantable medical device or medical material of claim 4, wherein the bone fastener is a stainless steel bone fastener.

6. A method for forming an antibacterial implantable medical device or medical material, comprising:

providing an implantable medical device or medical material, the implantable medical device or medical material having a surface;

forming a titanium coating on the implantable medical device or medical material;

growing titanium dioxide nanowires on the titanium coating;

treating the titanium dioxide nanowires with a nitrogen-containing gas and converting the titanium dioxide nanowires to titanium nitride nanowires extending from the titanium coating on the implantable medical device or medical material, wherein the titanium nitride nanowires are grown such that they extend at a selected angle from the titanium coating configured to exert a mechanical and electrical force on bacteria bilayer membranes sufficient to at least partially disrupt the bacteria bilayer membranes, and wherein the selected angle is between 60 degrees and 90 degrees.

7. The method of claim 6, wherein the titanium dioxide nanowires are synthesized by a wet oxidation process.

8. The method of claim 7, wherein converting the titanium dioxide nanowires comprises exposing the titanium dioxide nanowires to the nitrogen-containing gas at an elevated temperature.

9. The method of claim 6, wherein the selected angle is a 90 degree angle.

10. The method of claim 6, further comprising applying a charge to the titanium nitride coating and/or the titanium nitride nanowires.

11. The method of claim 6, wherein the implantable medical device is a bone fastener.

12. The method of claim 11, wherein the bone fastener is a stainless steel bone fastener.

* * * * *